United States Patent

Pattison

[11] 4,292,321
[45] Sep. 29, 1981

[54] 1,3,8-TRIAZASPIRODECANE-4-ONES, PHARMACEUTICAL COMPOSITIONS THEREOF AND METHOD OF USE THEREOF

[75] Inventor: Ian C. Pattison, Ann-Arbor, Mich.

[73] Assignee: Warner-Lambert Company, Morris Plains, N.J.

[21] Appl. No.: 111,043

[22] Filed: Jan. 10, 1980

Related U.S. Application Data

[63] Continuation of Ser. No. 42,175, May 24, 1979, abandoned.

[51] Int. Cl.³ .................. A61K 31/445; C07D 471/10; A61K 31/415
[52] U.S. Cl. ........................................ 424/267; 546/20; 546/19; 546/271; 546/217; 546/216; 546/290; 546/112; 546/297; 546/300; 546/229; 546/223; 546/199; 424/250; 544/253; 544/392; 544/394; 544/402; 544/398
[58] Field of Search .......................... 546/20; 424/267

[56] References Cited

U.S. PATENT DOCUMENTS

| | | | |
|---|---|---|---|
| 3,155,670 | 11/1964 | Janssen | 546/20 |
| 3,238,216 | 3/1966 | Janssen | 546/20 |
| 4,017,624 | 4/1977 | Maruyama et al. | 546/20 |
| 4,082,755 | 4/1978 | Van Wijngaarden et al. | 546/20 |

OTHER PUBLICATIONS

"Handbook of Chemistry and Physics," Forty-Sixth Edition. (The Chemical Rubber Co.), p. D-77 (Robert C. Weast) Ed.-in-C.

*Primary Examiner*—Robert T. Bond
*Attorney, Agent, or Firm*—Stephen I. Miller

[57] ABSTRACT

Compounds of the formula

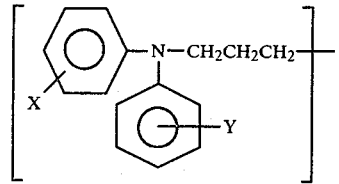

where Q is defined hereinafter and X and Y are hydrogen, halogen, lower alkyl, nitro are useful as neuroleptics.

8 Claims, No Drawings

1,3,8-TRIAZASPIRODECANE-4-ONES, PHARMACEUTICAL COMPOSITIONS THEREOF AND METHOD OF USE THEREOF

This is a continuation of application Ser. No. 42,175 filed May 24, 1979, now abandoned.

INTRODUCTION

This invention relates to compounds and derivatives of diphenylpropanamines which can be used as neuroleptics to treat schizophrenia and related ailments.

U.S. Pat. No. 3,917,598 to Maruyama et al., issued Nov. 4, 1975 and U.S. Pat. No. 4,017,624 to Maruyama et al., issued Apr. 12, 1977 discloses N-(omega-amino)alkyl aniline derivatives which are useful as neuroleptic agents. Belgian Pat. No. 771,152, issued Apr. 13, 1978, discloses a diphenylamine derivative, useful as an antihistamine, where one phenyl group must contain a four or five carbon alkyl substituent. U.S. Pat. No. 3,856,797 to Arimura et al., issued Dec. 24, 1974, discloses 8-aminoalkyl-3-oxo-1-thia-4,8-diazaspiro[4,5]decanes and derivatives which are used in liver dysfunction. British Pat. No. 1,047,935, published Nov. 9, 1966 and assigned to the American Cyanamid Company, discloses 1-substituted and 4-substituted aminoalkylene piperazines, useful in inhibiting the growth of protozoa. U.S. Pat. No. 3,196,152 to Wright, Jr. et al., issued July 20, 1965, discloses substituted imidazolidines and imidazolidinethiones which are useful as tranquilizers.

It has now been found that certain novel amines and derivatives are useful as neuroleptic agents, i.e., useful in treating schizophrenia and related ailments in mammals.

Accordingly, it is an object of this invention to provide a unique and novel compound and non-toxic, pharmaceutically acceptable salts thereof designed to treat schizophrenia and related ailments in mammals.

It is also an object of this invention to provide a unique and novel method of synthesizing said compound and the non-toxic, pharmaceutically acceptable salts thereof.

It is another object of this invention to provide a pharmaceutical composition for treating schizophrenia and related ailments in mammals which comprises an effective amount of said compound and/or the non-toxic, pharmaceutically acceptable salts thereof, together with an inert pharmaceutical carrier therefor.

It is still another object of this invention to provide a method of treating schizophrenia and related ailments in mammals by administering an effective amount of said composition and/or the non-toxic, pharmaceutically acceptable salts thereof.

SUMMARY OF THE INVENTION

The present invention is directed to a compound of the formula

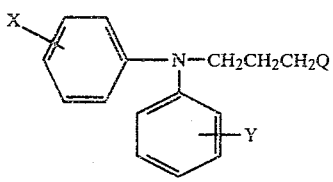
(I)

where $X$ is hydrogen, halogen, lower alkyl, nitro;
$Y$ is hydrogen, halogen, lower alkyl, nitro; and
$Q$ is

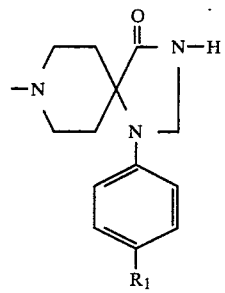
(II)

where $R_1$ is hydrogen, halogen, lower alkyl, lower alkoxy;

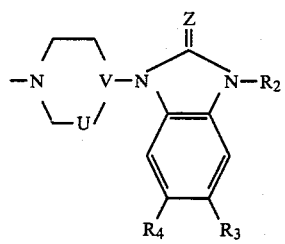
(III)

where $U-V$ is $-CH=C-$, $-CH_2-CH-$; $Z$ is oxygen, sulfur; $R_2$ is hydrogen, lower alkyl; $R_3$ is hydrogen, halogen, lower alkyl, lower alkoxy, trifluoromethyl; $R_4$ is hydrogen, halogen lower alkyl, lower alkoxy, trifluoromethyl;

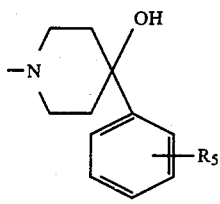
(IV)

where $R_5$ is hydrogen, halogen, lower alkyl, trifluoromethyl;

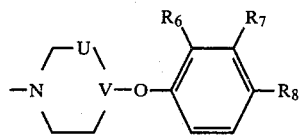
(V)

where $R_6$ is hydrogen, halogen, lower alkyl, lower alkoxy, trifluoromethyl; $R_7$ is hydrogen, halogen, lower alkyl lower alkoxy, trifluoromethyl; $R_9$ is hydrogen, halogen, lower alkyl, lower alkoxy, trifluoromethyl;

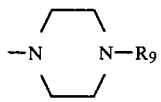

where R$_9$ is benzyl, phenyl,
p-fluorophenyl, o-methoxyphenyl,
o-(isopropylthio)phenyl, o-(n-
propylthiophenyl), 3-[N,N-diphenyl-
amino]-1-propyl, 2-hydroxyethyl,
2-quinoxalinyl,

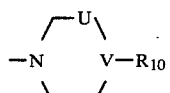

where R$_{10}$ is m-fluorophenyl,
m-methylphenyl, p-fluoroanilino,
alpha-hydroxybenzyl, p-chloro-
benzoyl;

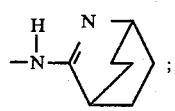

and the non-toxic, pharmaceutically acceptable salts thereof.

The present invention is also directed to a method of synthesizing this compound and the non-toxic, pharmaceutically acceptable salts thereof. Additionally, the present invention is directed to a pharmaceutical composition for treating schizophrenia and related ailments in mammals comprising an effective amount of this compound and/or the non-toxic pharmaceutically acceptable salts thereof together with an inert pharmaceutical carrier therefor. "Effective amount" means an amount sufficient to bring about the desired neuroleptic effect. "Lower alkyl" and "lower alkoxy" mean alkyl and alkoxy chains from one to seven carbon atoms in length. The present invention is also directed to a method of treating schizophrenia and related ailments in mammals by administering an effective amount of this compound and/or the non-toxic, pharmaceutically acceptable salts thereof.

DETAILED DESCRIPTION OF THE INVENTION

Compounds of the present invention, with the exception of the compound of formula (X)

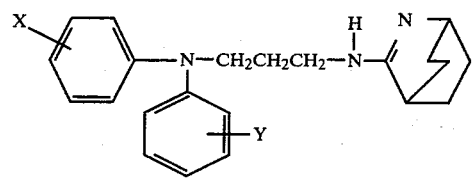

may be prepared according to the following reaction scheme (all symbols carry the same connotation as in the Summary):

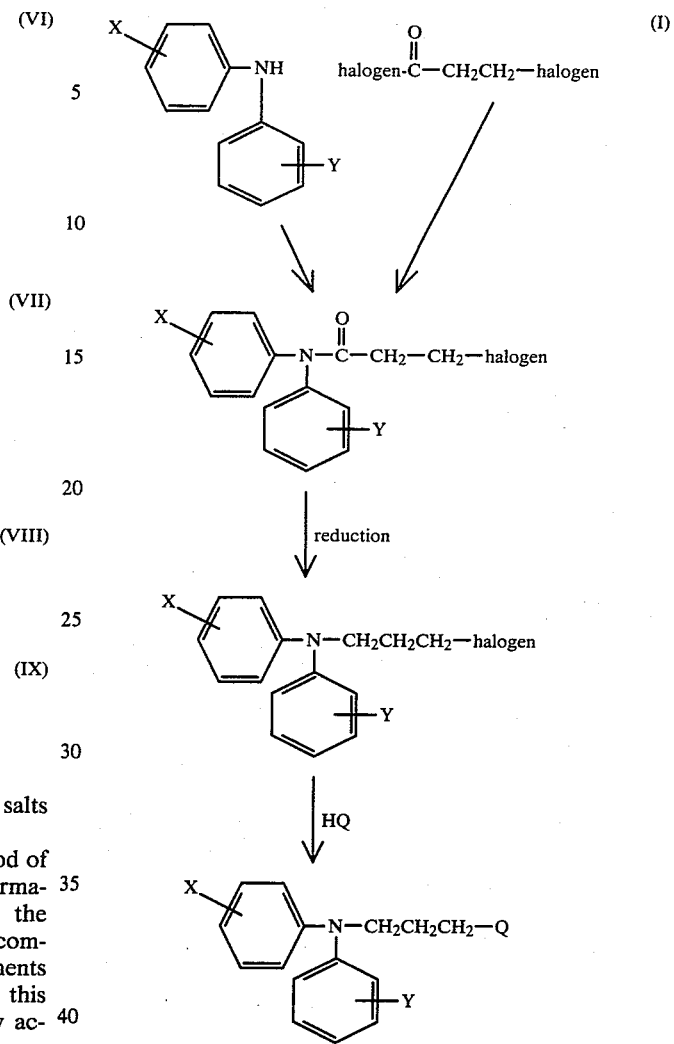

Referring to the reaction scheme, initially a diaryl secondary amine is condensed with a 3-halopropionyl halide in a variety of inert solvents. These diaryl secondary amines and 3-halopropionyl halides are conventionally available from known sources or may be prepared by known procedures. For example, diphenylamine, 4-nitrodiphenylamine, and 3-methyldiphenylamine are all available from the Aldrich Chemical Company in Milwaukee, Wisconsin, as are 3-bromopropionyl chloride and 3-chloroproprionyl chloride. Preparation of di-(4-fluorophenyl)amine is described by F. Benington, E. V. Shoop, and R. H. Poirer, *J. Org. Chem.* 18: 1506 (1953) and by Leonard and Sutton, *J. Am. Chem. Soc.* 70: 1564 (1948). Preparation of N-phenyl-N-(p-fluorophenyl)amine is described by Lichtenberger and Thermet, *Bull. Soc. Chim. France* 1951: 318. Preparation of N-(o-fluorophenyl)-N-(p-fluorophenyl)-amine is accomplished by an analogous procedure to the one described by Benington et al. in *J. Org. Chem.* 18: 1506 (1953).

Approximately one to three moles of diaryl secondary amine is condensed with about one to about three moles of 3-halopropionyl halide. The temperature and duration of this condensation may be varied over a wide range, and the reaction may be carried out in the presence or in the absence of a deacidifying agent. Preferably, this reaction is carried out by refluxing in benzene solvent in the absence of a deacidifying agent, with a slight molar excess of 3-halopropionyl halide. Hydrogen halide is evolved during the reaction, which is essentially complete within about three hours. The reaction product is then isolated as the free base by evaporating the remaining solvent. This condensation of a diaryl secondary amine with a 3-halopropionyl halide forms an N,N-diaryl-3-halopropionamide.

This N,N-diaryl-3-halopropionamide is then, in turn, reduced by the standard methods of reducing amides to amines. Reduction may be carried out with diborane in a suitable solvent over a wide range of conditions. The reaction is preferably run with an excess of diborane (up to about 1.5 moles per mole of amine) in the solvent tetrahydrofuran at about 10°–15° C., and is essentially complete within about 16 hours. The product may then be isolated by cautious addition of methanol with subsequent evaporation of solvent. This reduction of the N,N-diaryl-3-halopropionamide forms an N,N-diaryl-3-halopropanamine.

This diaryl-3-halopropanamine is further condensed with a compound of the formula HQ, where Q has the meaning described supra, (except for 2azabicyclo[2,2,-2]oct-2-en) to form a diaryl propanamine of the final structure (formula I):

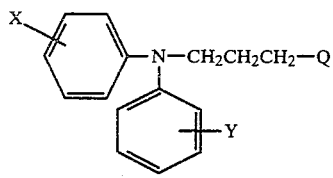

Approximately one to three moles of diaryl-3-halopropanamine is condensed with about one to about three moles of the compound HQ.

Compounds of the formula HQ are generally available from known chemical sources or may be prepared by known procedures in the literature. For example, 1-(4-aryl)-1,3,8-triazaspiro[4,5]decane-4-ones (formula II) are prepared by a procedure analogous to the one described in U.S. Pat. No. 3,155,670 to Janssen, issued Nov. 3, 1964. 4-(2-keto-1-benzimidazolinyl)piperidines (formula III) are generally prepared by a procedure analogous to the one described in U.S. Pat. No. 3,989,707 to Janssen, issued Nov. 2, 1976. Piperazine derivatives (formula VI) and 1,4-dioxa-8-azaspiro[4,5]-decanes (formula VIII) are generally available from the Aldrich Chemical Company in Milwaukee, Wis.

1-[1,2,3,6-tetrahydro-4-pyridyl]benzimidazol-2-ones (formula III) may be prepared in accordance with the procedure disclosed in U.S. Pat. No. 3,161,645 to Janssen, issued Dec. 15, 1964, and at Helv. Chim. Acta 43: 1298 (1960). 4-Piperidinyl-1,3-dihydro-2H-benzimidazole-2-thiones and 1-[1,2,3,6-tetrahydro-4-pyridyl]benzimidazole-2-thiones (formula III) may be prepared in accordance with the procedure disclosed in U.S. Pat. No. 3,963,727 to Ueno et al., issued Jan. 15, 1976. 4-Aryl-4-piperidinols (formula IV) are prepared by a procedure analogous to the one described in British Pat. No. 881,893 to Janssen, published Nov. 8, 1961. Synthesis of 4-aryloxypiperidines (formula V) is described in U.S. Pat. No. 3,260,723 to L'Italien and Campbell, issued July 12, 1966, while 4-aryloxy-1,2,3,6-tetrahydropyridines may be synthesized by a procedure analogous to the one in U.S. patent application Ser. No. 922,512 (Wise et al.) filed July 10, 1978.

This condensation reaction is usually carried out in a solvent such as an alcohol, an amine, a ketone, an aromatic hydrocarbon, an ether, an ester, and mixtures thereof, in the presence of a deacidifying agent such as an alkali metal carbonate, an alkali metal carbonate, an alkali metal hydroxide, an alkali metal alkoxide, a tertiary amine, an excess of HQ and mixtures thereof. Particularly preferred alcohols include methanol, ethanol 2-propanol, butanol, and mixtures thereof. Particular preferred amides include dimethylformamide, diethylformamide, dimethylacetamide and mixtures thereof. Suitable ketones include methylethyl ketone, methyl isobutyl ketone and mixtures thereof. Suitable aromatic hydrocarbons include benzene, toluene, xylene, and mixtures thereof. Suitable esters include dioxane, tetrahydrofuran, and mixtures thereof. Suitable esters include ethyl acetate, butyl acetate, and mixtures thereof. Suitable alkyl metal carbonates include sodium carbonate, potassium carbonate and mixtures thereof, While suitable alkali metal bicarbonates include potassium bicarbonate, sodium bicarbonate and mixtures thereof. Suitable alkali metal hydroxides include sodium hydroxide, potassium hydroxide and mixtures thereof, while suitable alkali metal alkoxides include sodium methoxide, potassium methoxide and mixtures thereof. Suitable tertiary amines include triethylamine, N,N-dimethylaniline, N,N-diethylaniline, pyridine, and mixtures thereof.

The reaction medium is heated at a temperature in the range from about room temperature to about the boiling point of the particular solvent employed for a period of from about two to about 24 hours. A small quantity of an accelerating agent, such as sodium iodide, may be included in the reaction medium. Preferred reaction conditions may vary with the nature of the compound HQ and the diaryl-3-halopropanamine. The final reaction product may be further processed and purified by conventional means such as recrystallization to obtain the final compound in pure form.

Certain compounds of the present invention may be prepared by alternate processes (all symbols carry the same connotation as in the Summary). For example, a diaryl-3-halopropanamine may be condensed with a 4-phenoxypyridine of the formula

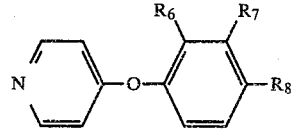

where $R_6$, $R_7$, and $R_8$ have the same meanings as listed supra. Preparation of these 4-phenoxypyridines is described at D. E. Butler et al., J. Med. Chem. 14: 75 (1971). Generally, about one to about three moles of diaryl-3-halopropanamine may be condensed with about one to about three moles of appropriate 4-phenoxypyridine in a suitable organic solvent. Suitable solvent may be selected from the group consisting of an alcohol, an amide, a ketone, an aromatic hydrocarbon, an ether, an ester, and mixtures thereof. A catalyst, such as sodium iodide, may be employed in this condensation. The reaction medium is heated to a temperature between about 25° C. and about the reflux temperature of the solvent, for about two to about twenty-four hours, until the condensation is complete. The compound produced by the condensation of a diaryll-3-halopropanamine and a 4-phenoxypyridine is a 4-phenoxy-1-[(diarylamino)propyl]pyridinium halide of the formula

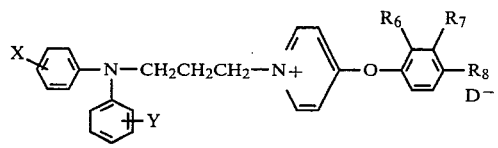

where D⁻ is the associated anion. This 4-phenoxy-1-[(diphenylamino)propyl]pyridinium halide may be partially reduced to the appropriate 3,6-dihydro-4-phenoxy-N,N-diaryl-1(2H)-pyridinepropanamine of the formula V:

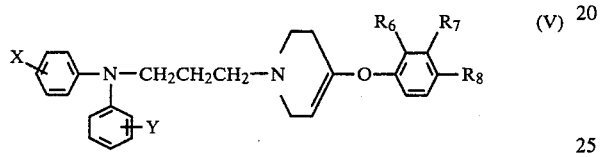

This partial reduction is accomplished with about 0.67 to about 2.0 molar equivalents of an alkali metal borohydride (e.g., potassium borohydride) in a suitable organic solvent. Suitable organic solvents include the group of lower alkanols such as methanol. Partial reduction is accomplished at a temperature between about 25° C. and about 60° C., for about one to about 16 hours.

This 3,6-dihydro-4-phenoxy-N,N-diphenyl-1(2H)-pyridinepropanamine may be further reduced to form the appropriate N,N-diaryl-4-phenoxy-1-piperidinepropanamine of the formula (V):

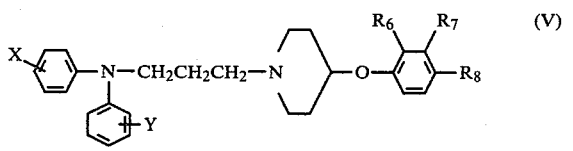

This further reduction is accomplished by agitation under pressure of about zero to about 200 pounds per square inch of hydrogen, in the presence of a suitable catalyst and solvent. This solvent may be selected from the group consisting of amides, alcohols, ether, esters, ketones and mixtures thereof. Suitable catalysts include the noble metal catalysts, such as platinum and palladium. This reduction is preferably run at a temperature between about 25° C. and about 50° C. until hydrogen uptake has reached about one mole.

The 4-aryloxy-1[(diarylamino)propyl]pyridinium halides may also be directly reduced to the corresponding N,N-diaryl-4-aryloxy-1-piperidine propanamines by catalytic hydrogenation using a noble metal catalyst such as platinum oxide or a nickel catalyst in a solvent such as ethanol or acetic acid. This direct route of reduction is described at page 46 of Klingsberg, *Pyridine and Its Derivatives Part Two*, Interscience Publishers, Inc., New York (1961).

The compound of the formula IX

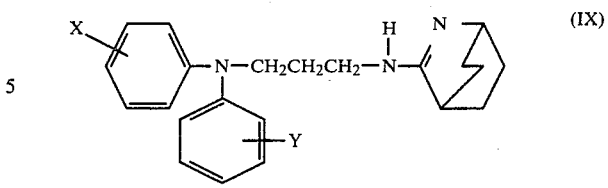

is produced by reacting the appropriate 3-(N,N-diarylamino]-1-aminopropane with 2-aza-3-ethoxybicyclo[2,2,2]oct-2-en in a lower alkanol solvent such as ethanol. About one to about three moles of 3-[N,N-diarylamino]-1-aminopropane are reacted with about one to about three moles of 2-aza-3-ethoxybicyclo[2,2,2]oct-2-en with the reaction medium being heated to a temperature between about 25° C. and about 100° C. for about six to about twenty-four hours. The reaction mixture may advantageously be heated in a steam bath so that the solvent distills away. 2-Aza-3-ethoxy-bicyclo[2,2,2]oct-2-en is produced by the condensation of 3-isoquinuclidone with from about one to about three equivalents of triethyloxonium tetrafluoroborate in a wide range of suitable inert solvent such as methylene chloride. The reaction mixture is stirred at a temperature between about 0° C. and about 60° C. for about six to about twenty four hours.

The 3-[N,N-diarylamino]-1-aminopropane may, in turn, be produced by the reaction of a diaryl-3-halopropanamine with potassium phthalimide, followed by treatment of the reaction product with hydrazine hydrate. About one to about three moles of diaryl-3-halopropanamine may be reacted with about one to about three moles of potassium phthalimide in a suitable organic solvent which is preferably selected from the group of dipolar aprotic solvents such as dimethyl formamide. The reaction medium is heated to a temperature between about 25° C. and about the reflux temperature for about one quarter to about sixteen hours. After isolation of the resulting product, a suitable solvent is added. This solvent is preferably selected from the group of lower alkanols such as methanol. About one to about three moles of hydrazine hydrate is added to the resulting solution. The solution is then heated for about one to about twenty four hours to a temperature between about 25° C. and about the reflux temperature of the particular solvent medium. The resulting product so formed is the appropriate 3-[N,N-diarylamino]-1-aminopropane.

The compound of formula (III) where Z is sulfur:

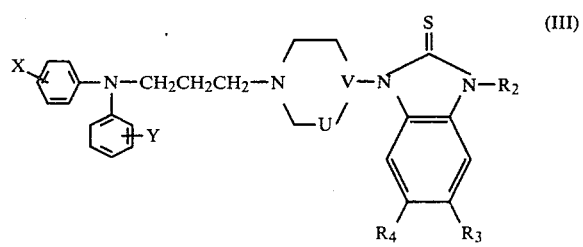

is produced from the corresponding compound of formula (III) where Z is oxygen

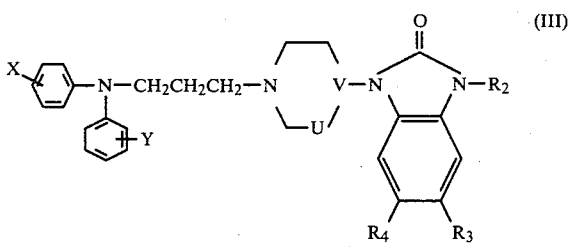

by refluxing for several hours with a sulfurating agent, in a suitable solvent.

Preferred sulfurating agents are selected from the group consisting of diphosphorus pentasulfide, tetraphosphorus trisulfide, tetraphosphorus heptasulfide, potassium sulfide, zinc sulfide, ammonium hydrosulfide, and mixtures thereof, while the preferred solvent is selected from the group consisting of organic solvents such as benzene, toluene, xylene, tetrahydrofuran, pyridine, and mixtures thereof. Especially preferred sulfurating agent is phosphorus pentasulfide and especially preferred solvent is pyridine. The reaction is heated from about one to about forty hours at a temperature between about room temperature and about the reflux temperature of the particular solvent.

N,N-diaryl-1,4-dioxo-8-azaspiro[4,5]decane-8-propanamine compounds of the present invention (formula VIII),

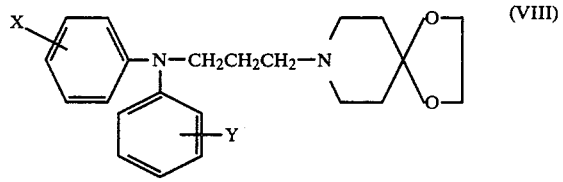

may be hydrolyzed in a mineral acid such as 1N (one normal) hydrochloric acid, or in a combination of a mineral acid with a lower alkanol solvent such as methanol, to form the appropriate 1-(3[bis(aryl)amino]-propyl)-4-piperidone of the formula

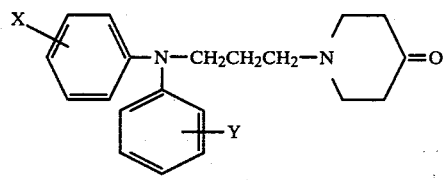

Hydrolysis is accomplished by heating the reaction mixture to a temperature between about 25° C., up to about the boiling point of the solvent, for about one to about sixteen hours, until evidence of the starting material is no longer visible by thin layer chromatography.

The 1-(3-[bis(aryl)amino]propyl)-4-piperidone may then be treated with a Grignard reagent in an ethereal solvent. Suitable Grignard reagents include appropriately substituted aryl magnesium chlorides, bromides iodides, and mixtures thereof, and suitable ethereal solvent is selected from the group consisting of ethyl ether, tetrahydrofuran, dioxane and mixtures thereof. A particularly preferred Grignard reagent is the appropriately substituted phenylmagnesium bromide. A particularly preferred ethereal solvent is ethyl ether. The reaction medium is heated to a temperature between about room temperature and about the boiling point of the solvent for about one-half to about three hours. The Grignard reaction forms the appropriate 1-[3-(diarylamino)propyl]-4-aryl-4-piperidinol of the formula:

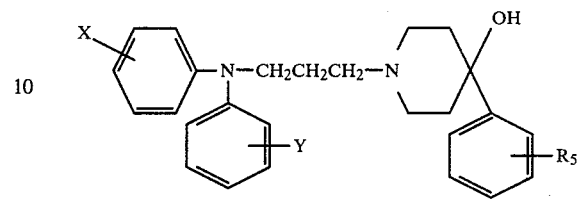

The structures of all products and intermediates are supported by appropriate microanalytical and/or spectroscopic (ir, nmr, uv) analyses. Compounds of the present invention may exist in anhydrous, hydrated, or partially hydrated forms. Anhydrous, hydrated, and partially hydrated forms are equivalent for the purpose of the present invention. Compounds of the present invention may also exist in solvated or partially solvated forms which are equivalent to the anhydrous form for purposes of the present invention.

The compounds of this invention may exist in the free base form, or in the form of an acid-addition salt. Non-toxic, pharmaceutically acceptable salts are formed by the reaction of the free base with any of the number of inorganic or organic acids, including hydrochloric, hydrobromic, hydriodic, sulfuric, nitric, phosphoric, acetic, benzoic, citric, maleic, malic, tartaric, succinic, gluconic, ascorbic, sulphamic, oxalic, pamoic, methane sulfonic, benzene sulfonic, and related acids and mixtures thereof. The free base compounds and their salts may differ in certain physical properties, such as solubility in polar solvents, but are otherwise equivalent for purposes of this invention.

The compounds of this invention are useful because of their valuable pharmacological properties. In general, these compounds possess interesting and significant activity as neuroleptic agents (i.e., for the treatment of schizophrenia). As with other known neuroleptics, the compounds of this invention readily displace $^3$H-haloperidol from dopamine receptor binding sights in the $^3$H-haloperidol receptor binding assay (HRBA). This screen is a most effective in vitro method for detecting neuroleptic agents and correlates well with human clinical doses. The HRBA screen is described by I. Creese, D. R. Burt and S. H. Snyder, *Science* 142: 480 (1976) and by B. Seeman, T. Lee, M. Chani-Wong and K. Wong, *Nature* 261: 717 (1967). A test compound is considered to be an active neuroleptic in this test if it shows approximately 30% of $^3$H-haloperidol binding at 100 n moles.

The compounds of the present invention, and/or the non-toxic, pharmaceutically acceptable salts thereof, may be administered to mammals in pharmaceutical formulations comprising the compounds of the invention, and/or the non-toxic, pharmaceutically acceptable salts thereof, together with a pharmaceutically acceptable, non-toxic carrier. The compositions of the present invention may be administered parentally in combination with conventional injectable liquid carriers selected from the group consisting of sterile pyrogen-free water, sterile peroxide-free ethyl oleate, dehydrated alcohols, propylene glycol, and mixtures thereof. Suitable pharmaceutical adjuvants for the injecting solutions include stabilizing agents, solubilizing agents, buffers and viscosity regulators. Several of these adjuvants are selected from the group consisting of ethanol, ethylene diamine tetra-acetic acid, tartrate buffers, citrate buffers, and high molecular weight polyethylene oxide viscosity regulators. These pharmaceutical formulations may be injected intramuscularly, intraperitoneally, or intravenously.

The compounds of the present invention, and/or the non-toxic, pharmaceutically acceptable salts thereof, may be administered to mammals orally in combination with conventionally compatible carriers in solid or in liquid form. These oral compositions may contain conventional ingredients such as binding agents selected from the group consisting of syrups, acacia, gelatin, sorbitol, tragacanth, polyvinylpyrrolidone, and mixtures thereof. These oral compositions may include fillers selected from the group consisting of lactose, mannitols, starch, calcium phosphate, sorbitol, methylcellulose, and mixtures thereof. These compositions may also contain lubricants such as magnesium stearate, high-molecular weight polymers such as polyethylene glycol, high-molecular weight fatty acids such as stearic acid or silica, disintegrants such as starch, and wetting acids such as sodium lauryl sulfate.

The oral compositions may take any convenient form such as tablets, capsules, lozenges, aqueous or oily suspensions, emulsions, or even dry products which may be reconstituted with water and/or any other liquid medium before use. The solid or liquid oral forms may contain flavors, sweeteners, preservatives such as alkyl p-hydroxybenzoates. The liquid forms may contain suspending agents such as sorbitol, glucose or other sugar syrups, methyl, hydroxymethyl, carboxymethyl cellulose, and gelatin, emulsifying agents such as lecithin or sorbitan monooleate, and conventional thickening agents. The liquid composition may optionally be encapsulated in capsules, for example gelatin capsules, in an effective amount.

The dosage levels of the compositions of the present invention will depend on the nature and severity of the biological ailment to be considered, as well as on the path of administration. The compositions of the present invention may be administered in dosages generally from about 1 mg/kg to about 1000 mg/kg, typically from about 2 mg/kg to about 500 mg/kg and most typically from about 3 mg/kg to about 200 mg/kg. The age, weight, and health of the patient will have to be taken into account when determining optional dosage levels to be administered.

EXAMPLE 1

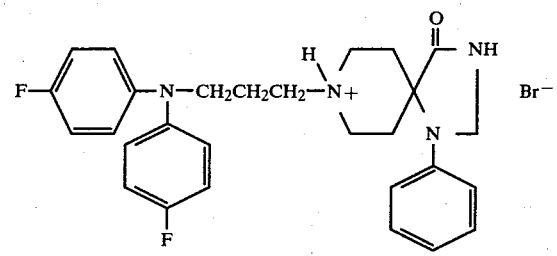

8-[3-(Bis-[4-fluorophenyl]amino)propyl]-1-phenyl-1,3,8-triazaspiro[4,5]decan-4-one hydrobromide 3-[N,N-di(4-fluorophenylamino)]-1-bromopropane is prepared from the reaction of N,N-di(4-fluorophenyl)amine with 3-bromopropionyl chloride followed by reduction with borane in tetrahydrofuran by a procedure analogous to the preparation of 3-[N,N-diphenylamino]-1-bromopropane in Example 2. Preparation of N,N-di(4-fluorophenyl)amine is described by Leonard and Sutton, J. Am. Chem. Soc. 70: 1564 (1948).

A mixture of 7.1 g. (0.022 moles) of 3-[N,N-di(4-fluorophenylamino)]-1-bromopropane, 10.0 g (0.0432 moles) of 1-phenyl-1,3,8-triazaspiro-[4,5]decan-4-one (available from the Aldrich Chemical Company, Milwaukee, WI) and 3.1 g. (0.021 moles) of sodium iodied in 80 ml. of methyl ethyl ketone is refluxed for about 16 hours, cooled and filtered. The mother liquor is evaporated and the residue triturated with carbon tetrachloride and filtered. The combined filter cakes are slurried in water and filtered and the filter cake recrystallized from dimethylformamide and then with acetic acid to give 1.3 g. of 8-[3-(bis[4-fluorophenyl]amino)propyl]-1-phenyl-1,3,8-triazaspiro[4,5]decan-4-one hydrobromide, mp. 289.5° C.

8-[3-(Bis[4-fluorophenyl]amino)propyl]-1-phenyl-1,3,8-triazaspiro[4,5]decan-4-one shows approximately 73% inhibition of $^3$H-haloperidol binding at 10 n moles concentration and approximately 77% inhibition of $^3$H-haloperidol binding at 100 n moles concentration in the $^3$H-Haloperidol Recepter Binding Assay (HRBA).

EXAMPLE 2

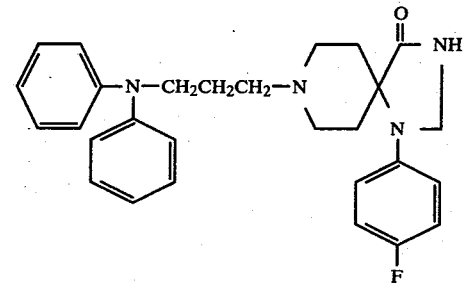

8-[3-(Diphenylamino)propyl]-1-(4-fluorophenyl)-1,3,8-triazaspiro[4,5]decan-4-one A solution of 449 g. (2.65 moles) of diphenylamine and 500 g. (2.92 moles) of 3-bromopropionyl chloride in 3.1 of toluene is refluxed for 1 hours, trapping the hydrogen chloride which is evolved. The reaction mixture is evaporated and the residue twice recrystallized from isopropanol to give 706 g. of 3-bromo-N,N-diphenyl-propionamide, mp. 97°–99° C.

A solution of 304 g. (1.00 moles) of 3-bromo-N,N-diphenyl propionamide in 800 ml. of tetrahydrofuran is stirred and maintained at −3° C. to −1° C. while adding 1.1 l. of a 1 molar solution of borane in tetrahydrofuran over a period of 15 minutes. The reaction is allowed to gradually warm to 21° C. over a period of about 1.75 hours and refluxed for a period of about 10 minutes. The reaction mixture is then treated dropwise with 50 ml. of methanol. After gas evolution ceases, solvent is removed under vacuum. The oily residue is dissolved in cyclohexane, washed with 20% caustic solution and then with water, dried and passed through a column of about 400 g. of silica gel, eluting with cyclohexane, to give 3-[N,N-diphenylamino]-1-bromopropane.

A mixture of 3.3 g. (0.0114 moles) of 3-[N,N-diphenylamino]-1-bromopropane, 2.8 g. (0.0114 moles) of 1-[4-fluorophenyl]-1,3,8-triazaspiro[4,5]-decan-4-one, 1.2 g. (0.0114 moles) of sodium carbonate and 0.2 g. of sodium iodide in 35 ml. of methyl ethyl ketone is refluxed for about 16 hours. The preparation of 1-[4-fluorophenyl]-1,3,8-triazaspiro[4,5]decan-4-one is accomplished by a procedure analogous to the one described in U.S. Pat. No. 3,155,670 to Janssen, issued Nov. 3, 1964. Solvent is removed under vacuum and the residue is dissolved in chloroform, washed with water, and chromatographed on a silica gel column. The combined product fractions are evaporated under vacuum and the residue twice recrystallized from ethanol giving 1.96 g. of 8-[3-(diphenylamino)propyl]-1-(4-fluorophenyl)-1,3,8-triazaspiro[4,5]decan-4-one, mp. 161.5°–163.5° C.

8-[3-(Diphenylamino)propyl]-1,3,8-triazaspiro[4,5]decan-4-one shows approximately 76% inhibition of $^3$H-haloperidol binding at 10 n moles concentration and approximately 85% inhibition of $^3$H-haloperidol binding at 100 n moles concentration in the $^3$H-Haloperidol Receptor Binding Assay.

EXAMPLE 3

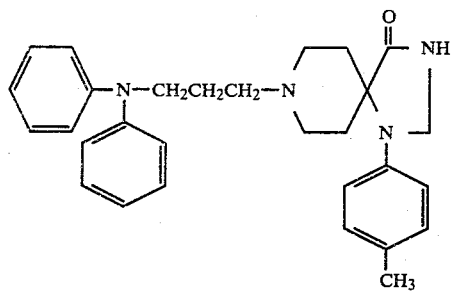

8-[3-(Diphenylamino)propyl]-1-(4-methylphenyl)-1,3,8-triazaspiro[4,5]decan-4-one A mixture of 3.54 g. (0.0122 moles) of 3[N,N-diphenylamino]-1-bromopropane (prepared according to the procedure of Example 2), 3.0 g. (0.0122 moles) of 1-(4-methylphenyl)-1,3,8-triazaspiro[4,5]-decan4-one, 1.3 g. (0.0122 moles) of sodium carbonate and 0.2 g. of sodium iodied in 35 ml. of methyl ethyl ketone is refluxed for about 16 hours. The preparation of 1-(4-methylphenyl)-1,3,8-triazaspiro[4,5]decan-4-one is described in U.S. Pat. No. 3,155,670 to Janssen, issued Nov. 3, 1964. Solvent is removed under vacuum and the residue is dissolved in chloroform, washed with water and then chromatographed on a column of silica gel. The combined product fractions are evaporated and the residue is recrystallized from ethyl acetate giving 2.14 g. of 8-[3-(diphenylamino)propyl]-1-(4-methylphenyl)-1,3,8-triazaspiro[4,5]decan-4-one, mp. 177°–178° C.

8-[3-(Diphenylamino)propyl]-1-(4-methylphenyl)-1,3,8-triazaspiro[4,5]-decan-4-one shows approximately 71% inhibition of $^3$H-haloperidol binding at 10 n moles concentration and approximately 87% inhibition of $^3$H-haloperidol binding at 100 n moles concentration in the $^3$H-Haloperidol Receptor Binding Assay.

EXAMPLE 4

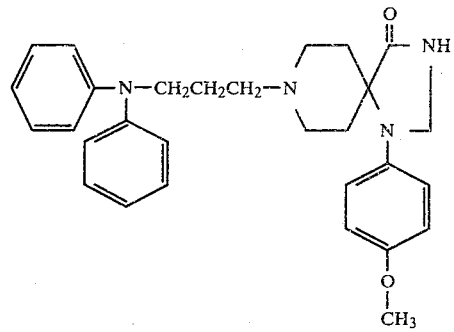

8-[3-(Diphenylamino)propyl]-1-(4-methoxyphenyl)-1,3,8-triazaspiro[4,5]decan-4-one A mixture of 940 mg. (0.00325 moles) of 3-[N,N-diphenylamino]-1-bromopropane (prepared according to the procedure of Example 2) and 850 mg. (0.00325 moles) of 1-(4-methoxyphenyl)-1,3,8-triazaspiro[4,5]decan-4-one, 400 mg. of sodium carbonate and 100 mg. of sodium iodide in 15 ml. of methyl ethyl ketone is refluxed for about 16 hours. The preparation of 1-(4-methoxyphenyl)-1,3,8-triazaspiro[4,5]decan-4-one is described in U.S. Pat. No. 3,155,670 to Janssen, issued Nov. 3, 1964. Solvent is evaporated and the residue is dissolved in chloroform, washed with water and chromatographed on a column of silica gel. The produce fractions are evaporated and the residue is recrystallized from isopropyl alcohol and again from ethanol, giving 470 mg. of 8-[3-diphenylamino)propyl]-1-(4-methoxyphenyl)-1,3,8-triazaspiro[4,5]decan-4-one, mp. 156.5°–157.5° C.

8-[3-(Diphenylamino)propyl]-1-(4-methoxyphenyl)-1,3,8triazaspiro[4,5]decan-4-one shows approximately 67% inhibition of $^3$H-haloperidol binding at 10 n moles concentration and approximately 98% inhibitions of $^3$H-haloperidol binding at 100n moles concentration in the $^3$H-Haloperido Receptor Binding Assay.

EXAMPLE 5

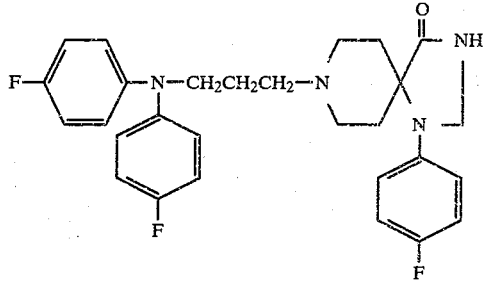

8-[3-[Bis-(4-fluorophenyl)amino]propyl]-1-(4-fluorophenyl)-1,3,8-triazaspiro[4,5]decan-4-one A mixture of 12.8 g. (0.0513moles) of 1-[4-fluorophenyl]-1,3,8-triazaspiro[4,5]decan-4-one (preparation described in U.S. Pat. No. 3,155,670 to Janssen, issued Nov. 3, 1964), 14.46 g. (0.0513 moles) of 3-[N,N-di(4-fluorophenylamino)]-1-chloropropane, 8.98 g. (0.065 moles) of potassium carbonate and 0.5 g. of sodium iodide in 150 ml. of methyl isobutyl ketone is refluxed for about 16 hours. Solvent is evaporated. Water is added and the product is extracted into chloroform. The chloroform is evaporated and the residue is recrystallized from toluene and then from isopropanol to give 13.4 g. of 8-[3-[bis-(4-fluorophenyl)amino]propyl]-1-(4-fluorophenyl)-1,3,8-triazaspiro[4,5]decan-4-one, mp. 161.5°–163.0° C. 8-[3-[Bis-(4-fluorophenyl)amino]-propyl]-1-(4-fluorophenyl)-1,3,8-triazaspiro[4,5]decan-4-one shows approximately 84% inhibition of $^3$H-haloperidol binding at 10 n moles concentration and approximately 100% inhibition of $^3$H-haloperidol binding at 100 n moles concentration in the $^3$H-Haloperidol Receptor Binding Assay.

EXAMPLE 6

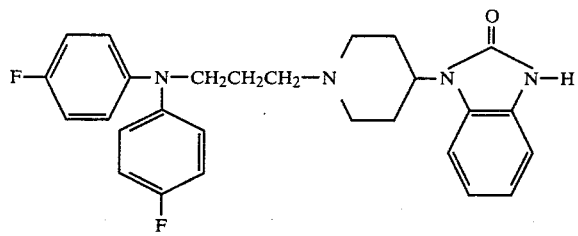

1-(1[3-[Bis(4-fluorophenyl)amino]propyl]-4-piperidyl)-1,3-dihydro-2H-benzimidazol-2-one 3-[N,N-di(4-fluorophenylamino)]-1-bromopropane is prepared form the reaction of N,N-di(4-fluorophenyl)amine with 3-bromopropionyl chloride followed by reduction with borane in tetrahydrofuran by a procedure analogous to the preparation of 3-[N,N-diphenylamino]-1-bromopentane in Example 2.

A mixture of 10.2 g. (0.031 moles) of 3-[N,N-di(4-fluorophenyl)amino]-1-bromopropane, 5.0 g. (0.023 moles) of 4-(2-keto-1-benzimidazolinyl)-piperidine (available from the Aldrich Chemical Company, Milwaukee, Wis., 3.2 g. (0.023 moles) of potassium carbonate and a few crystals of sodium iodide in 150 ml. of acetonitrile are refluxed for about 72 hours. The reaction mixture is filtered while still hot and the filtrate chilled. The resulting crystals are filtered and the mother liquor concentrated to give a second crop of crystals. The two crops are combined and recrystallized first from a mixture of chloroform and acetonitrile and then from ethyl acetate to give 4.0 g. of 1-(1-[3-[bis(4-fluorophenyl)amino]propyl]-4-piperidyl)-1,3-dihydro-2H-benzimidazol-2-one, mp. 183°–184° C.

1-(1-[3-[Bis(4-fluorophenyl)amino]-4-piperidyl)-1,3-dihydro-2H-benzimidazol-2-one shows approximately 50% inhibition of $^3$H-haloperidol binding at 1 n mole concentration and approximately 78% inhibition of $^3$H-haloperidol binding at 10 n moles concentration in the $^3$H-Haloperidol Receptor Binding Assay.

EXAMPLE 7

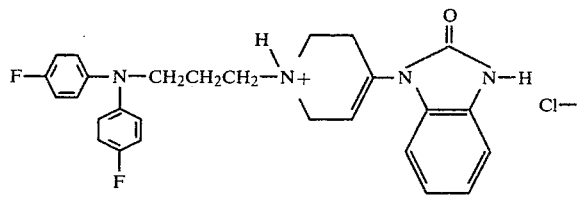

1-[1-[3-[Bis(4-fluorophenyl)amino]propyl]-1,2,3,6-tetrahydro-4-pyridinyl]-1,3-dihydro-2H-benzimidazol-2-one hydrochloride A mixture of 2.1 g. (0.0064 moles) of 3-[N,N-di(4-fluorophenylamino)]-1-bromopropane, 1.2 g. of 1,2,3,6-tetrahydro-4-benzimidazol-2-one, 0.59 g. of sodium carbonate and 0.5 g. of sodium iodide in 50 ml. of methyl ethyl ketone is refluxed for about six hours. The preparation of 1-[1,2,3,6-tetrahydro-4-pyridyl]benzimidazol-2-one is described in U.S. Pat. No. 3,161,645 to Janssen, issued Dec. 15, 1964 and at Helv. Chim. Acta 43: 1298 (1960). The hot reaction mixture is then filtered and the filtrate evaporated under vacuum. The residue is converted to the hydrochloride salt, crystallized from acetonitrile and recrystallized from aqueous ethanol to give 350 mg. of 1-[1-[3-bis(4-fluorophenyl)amino]propyl]-1,2,3,6-tetrahydro-4-pyridinyl]-1,3-dihydro-2H-benzimidazol-2-one hydrochloride, m.p. 257°–260° C.

1-[1-[3-[Bis(4-fluorophenyl)amino]propyl]-1,2,3,6-tetrahydro-4-pyridinyl]-1,3-dihydro-2H-benzimiazol-2-one shows approximately 22% inhibition of $^3$haloperidol binding at 10 n moles concentration and approximately 67% inhibition of $^3$H-haloperidol binding at 100 n moles concentration in the $^3$H-Haloperidol Receptor Binding Assay.

EXAMPLE 8

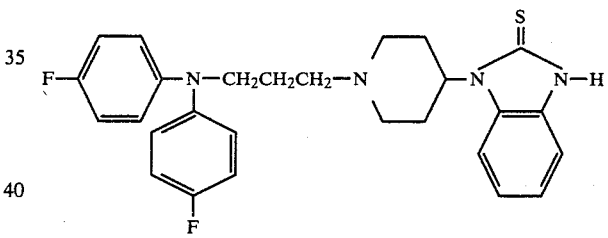

1-[1-(3-[Bis(4-fluorophenyl)amino]propyl)-4-piperidinyl]-1,3-dihydro-2H-benzimidazole-2-thione A mixture of 6.0 g. (0.0129 moles) of 1-[1-(2-[bis(4-fluorophenyl)amino]propyl)-4-piperidyl]-1,3-dihydro-2H-benzimidazol-2-one (preparation described in Example 5, supra) and 14.4 g. (0.065 moles) of phosphorous pentasulfide in 60 ml. of pyridine is refluxed for about 20 hours. The reaction mixture is cooled. Ice and dilute caustic are added. The product is extracted into chloroform, washed with water and passed through a column of silica gel. The eluate is evaporated and the residue is crystallized from acetone giving 2.0 g. of 1-[1-(3-[bis(4-fluorophenyl)amino]propyl)-4-piperidinyl]-1,3-dihydro-2H-benzimidazole-2-thione, mp. 191°–192° C.

1-[1-(3-[Bis(4-fluorophenyl)amino]propyl)-4-piperidinyl]-1,3-dihydro-2H-benzimidazole-2-thione may also be prepared in accordance with the procedure disclosed in Example 1, by the condensation of 3-[N,N-di(4-fluorophenylamino)]-1-bromopropane with 4-piperidinyl-1,3-dihydro-2H-benzimidazole-2-thione of the formula

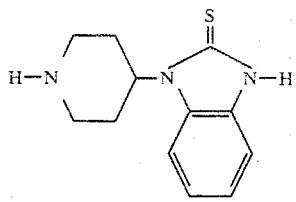

The synthesis of 4-piperidinyl-1,3-dihydro-2H-benzimidazole-2-thione is described in U.S. Pat. No. 3,963,727, to Ueno et al., issued Jan. 15, 1976.

1-[1-(3-[Bis(4-fluorophenyl)amino]propyl)-4-piperidinyl]-1,3-dihydro-2H-benzimidazole-2-thione shows approximately 28% inhibition of $^3$H-Haloperidol binding at 10 n moles concentration and approximately 89% inhibition of $^3$H-haloperidol binding at 100 n moles concentration in the $^3$H-Haloperidol Receptor Binding Assay.

EXAMPLE 9

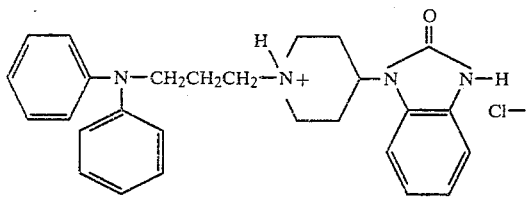

1-[1-(3-(Diphenylamino]propyl)-4-piperidinyl]-1,3-dihydro-2H-benzimidazol-2-one hydrochloride A mixture of 6.8 g. (0.031 moles) of 4-(2-keto-1-benzimidazolinyl)piperidine (available from the Aldrich Chemical Company, Milwaukee, Wis.), 4.6 g. (0.016 moles) of 3-[N,N-diphenylamino]-1-bromopropane and 2.35 g. of sodium iodide in 50 ml. of methyl ethyl ketone is refluxed for about 4.5 hours. Solvent is evaporated. The residue is taken up in methylene chloride and washed with dilute caustic. Solvent is again evaporated, the residue is converted to the hydrochloride salt, and then recrystallized from methanol, giving 3.5 g. of 1-[1-(3[diphenylamino]-propyl)-4-piperidinyl]-1,3-dihydro-2H-benzimidazol-2-one hydrochloride, mp. 289°–291° C.

1[1-(3-[Diphenylamino]propyl)-4-piperidinyl]-1,3-dihydro-2H-benzimidazol-2-one hydrochloride shows approximately 68% inhibition of $^3$H-haloperidol binding at 10 n moles concentration and approximately 91% inhibition binding at 100 n moles concentration in the $^3$H-Haloperidol Receptor Binding Assay.

EXAMPLE 10

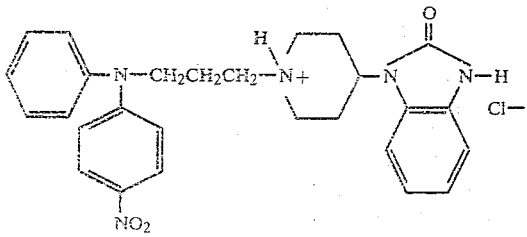

1,3-Dihydro-1-[1-(3-[(4-nitrophenyl)phenylamino]-propyl)-4-piperidinyl]-2H-benzimidazol-2-one hydrochloride 3-[N-phenyl-N-(4-nitrophenyl)amino]-1-bromopropane is prepared from N-phenyl-N-(4-nitrophenyl)amide with 3-bromopropionyl chloride, followed by reduction with borane in tetrahydrofuran, by a procedure analogous to the preparation of 3-[N,N-diphenylamino]-1-bromopropane in Example 2.

A mixture of 2.2 g. (0.0066 moles) of 3-[N-phenyl-N-(4-nitrophenyl)amino]-1-bromopropane, 2.9 g. (0.013 moles) of 4-(2-keto-1 benzimidazolinyl)piperidine (available from the Aldrich Chemical Company, Milwaukee, Wis.), and 1.0 g. of sodium iodide in 25 ml. of methyl ethyl ketone is refluxed for about 6 hours. Solvent is evaporated and the residue is taken up in methylene chloride and washed with dilute caustic. Solvent is again evaporated and the residue is converted to the hydrochloride salt, crystallized in isopropyl alcohol and recrystallized from methanol to give 1.1 g. of 1,3-dihydro-1-[1-(3-[(4-nitrophenyl)-phenylamino]propyl)-4-piperidinyl]-2H-benzimidazol-2one hydrochloride, mp. 275°–276° C.

1,3-Dihydro-1-[1-(3-[(4-nitrophenyl)phenylamino]-propyl) -4-piperidinyl]-2H-benzimidazol-2-one hydrochloride shows approximately 17% inhibition of $^3$H-haloperidol binding at 10 n moles concentration and approximately 75% inhibition of $^3$H-haloperidol binding at 100 n moles concentration in the $^3$H-Haloperidol Receptor Binding Assay.

EXAMPLE 11

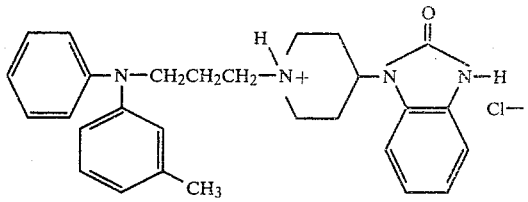

1,3-Dihydro-1-[1-(3-[(3-methylphenyl)phenylamino]-propyl-4-piperidinyl]-2H-benzimidazol-2-one hydrochloride 3-[N-phenyl-N-(3-methylphenyl)]amino-1-bromopropane is prepared by the reaction of N-phenyl-N-(3-methylphenyl)amine with 3-bromopropionyl chloride, followed by reduction with borane in tetrahydrofuran, by a procedure analogous to the preparation of 3-[N,N-diphenylamino]-1-bromopropane in Example 2.

A mixture of 5.3 g. (0.017 moles) of 3-[N-phenyl-N-(3-methylphenyl)]amino-1-bromopropane, 7.6 g. (0.035 moles) of 4-(2-keto-1benzimidazolinyl)piperidine (available from the Aldrich Chemical Company, Milwaukee, Wis.) and 2.6 g. of sodium iodide in 50. ml. of methyl ethyl ketone is refluxed for about 5 hours. Solvent is evaporated and the residue is taken up in methylene chloride and washed with dilute alkali. Solvent is evaporated. The residue is crystallized from 1N hydrochloric acid and then recrystallized from methanol to give 1.8 g. of 1,3-dihydro-1-[1-(3-[(3-methylphenyl)-phenylamino]propyl)-4-piperidinyl]-2H-benzimidazol-2-one hydrochloride, mp. 232°–234° C.

1,3-Dihydro-1-[1-(3-methylphenyl)phenylamino]-propyl)-4-piperidinyl]-2H-benzimidazol-2-one hydrochloride shows approximately 61% inhibition of $^3$H-haloperidol binding at 10 n moles concentration and approximately 91% inhibition of $^3$H-haloperidol binding at 100 n moles concentration in the $^3$H-Haloperidol Receptor Binding Assay.

EXAMPLE 12

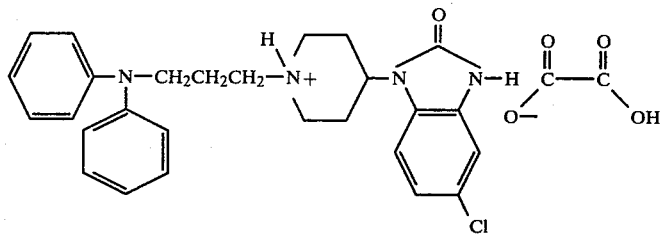

5-Chloro-1-[1-(3-[diphenylamino]propyl)-4-piperidinyl]-1,3-dihydro-2H-benzimidazol-2-one ethanedioate A mixture of 1.07 g. (0.00369 moles) of 3-[N,N-diphenylamino]-1-bromopropane, 0.93 g. (0.00369 moles) of 5-chloro-1,3-dihydro-1-(4-piperidinyl)-2H-benzimidazol-2-one, 0.4 g. (0.0038 moles) of sodium carbonate and 0.1 g. of sodium iodide in 15 ml. of methyl ethyl ketone is refluxed for about 16 hours. 5-Chloro-1,3-dihydro-1-(4-piperidinyl)-2H-benzimidazol-2-one is prepared by a procedure analogous to the one described in U.S. Pat. No. 3,989,707 to Janssen et al., issued Nov. 2, 1976. The solvent is evaporated and the residue dissolved in chloroform, washed with water, dried, and passed through a column of silica gel. The product fractions, which are eluted with ethyl acetate, are concentrated, converted to the oxalate salt in isopropanol. The resulting crystals are collected and recrystallized from isopropanol to give 0.50 g. of 5-chloro-1-[1-(3-[diphenylamino]propyl)-4-piperidinyl]-1,3-dihydro-2H-benzimidazol-2-one ethanedioate (1:1), mp. 200°–206° C.

EXAMPLE 13

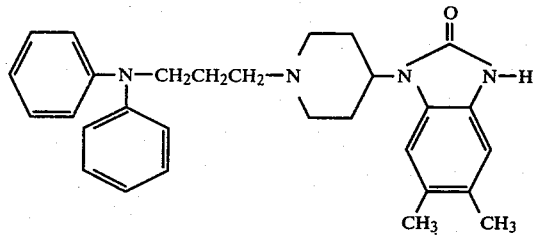

1-[1-(3-[Diphenylamino]propyl)-4-piperidiyl]-1,3-dihydro-5,6-dimethyl-2H-benzimidazol-2-one The preparation of 5,6-dimethyl-1,3-dihydro-1-(4-piperidinyl)-2H-benzimidazol-2-one is accomplished by hydrogenating 1-[1-benzyl-1,2,3,6-tetrahydro-4-pyridyl]-5,6-dimethyl-2-benzimidazolinone in an acetic acid-ethanol mixture with palladium catalyst in a similar manner to the one described at Rossi et al., *Helv. Chem Acta* 43: 1312 (1960), for the reduction of 1-[1,2,3,6-tetrahydro-4-piperidyl]-2H -benzimidazol-2-one. The preparation of 1[1-benzyl-1-[1-benzyl-1,2,3,6-tetrahydro-4-pyridyl]-5,6-dimethyl-2-benzimidazolinone is, in turn, described in U.S. Pat. No. 3,161,645 to Janssen, issued Dec. 15, 1964.

A mixture of 8.3 g. (0.034 moles) of 3-[N,N-diphenylamino]-1-chloropropane, 6.5 g. (0.026 moles) of 5,6-dimethyl-1,3-dihydro-1-(4-piperidinyl)-2H-benzmidazol-2-one, 4.2 g. (0.040 moles) of sodium carbonate and 0.5 g. of sodium iodide in 75 ml. of 4-methyl-2-pentanone is refluxed for about 20 hours. Solvent is evaporated and the residue is dissolved in water and chloroform. The product is extracted into chloroform and the resulting solution is passed through a column of silica gel. The column is washed with chloroform and the product eluted with chloroform-ethyl acetate. Product fractions are combined, evaporated, and the residue is recrystallized from chloroform-ethanol to give 3.4 g. of 1-[1-(3-[diphenylamino]propyl)-4-piperidyl]-1,3-dihydro-5,6-dimethyl-2H-benzimidazol-2-one, mp. 189.5°–191.5°.

1-[1-3[Diphenylamino]propyl)-4-piperidyl]-1,3-dihydro-5,6-dimethyl-2H-benzimidazol-2-one shows approximately 53% inhibition of $^3$H-haloperidol binding at 10 n moles concentration and approximately 93% inhibition of $^3$H-haloperidol binding at 100 n moles concentration in the $^3$H-Haloperidol Receptor Binding Assay.

EXAMPLE 14

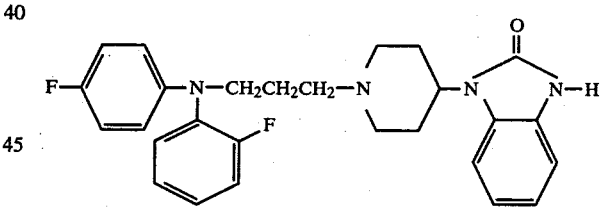

1,3-Dihydro-1-[1-[3-[(4-fluorophenyl)-(2-fluorophenyl)amino] propyl]-4-piperidinyl]-2H-benzimidazol-2-one 3-[N-(o-fluorophenyl)-N-(p-fluorophenyl)]-1-chloropropane is prepared by the reaction of N-(o-fluorophenyl)-N-(p-fluorophenyl)amine with 3-chloropropionyl chloride, followed by reduction with borane in tetrahydrofuran by a procedure analogous to the preparation of 3-[N,N-diphenylamino]-1-bromopropane in Example 2. N-(o-fluorophenyl)-N-(p-fluorophenyl)amine is, in turn, prepared by the Chapman rearrangement of p-fluorophenyl-N-(o-fluorophenyl)benzimidate, followed by hydrolysis of the resulting amide by a procedure analogous to the procedure of Benington et al., *J. Org Chem.* 18: 1506 (1953), for preparation of the isomeric di(4-fluorophenyl)amine. A mixture of 7.8 g. (0.028 moles) of 3-[N-(o-fluorophenyl)-N-(p-fluorophenyl)]-1-chloropropane, 6.0 g. (0.028 moles) of 4-(2-keto-1-benzimidazolinyl)piperidine (available from the Aldrich Chemical Company, Milwaukee, Wis.), 4.6 g.

(0.033 moles) of potassium carbonate and 0.8 g. of sodium iodide in 65 ml. of 4-methyl-2-pentanone is refluxed for about 21 hours. Solvent is then evaporated. Water is added to the residue and the product is extracted into chloroform. The chloroform is evaporated and the residue is recrystallized once from ethyl acetate and again from ethylacetate-isopropanol to give 5.9 g. of 1,3-dihydro-1-[1-[3-[(4-fluorophenyl)-(2-fluorophenyl)amino]propyl]-4-piperidinyl]-2H-benzimidazol-2-one, mp. 168°–169° C.

1,3-Dihydro-1-[1-[3-[(4-fluorophenyl)-(2-fluorophenyl)amino]propyl]-4-piperidinyl]-2H-benzimidazol-2-one shows approximately 56% inhibition of $^3$H-haloperidol binding at 1 n mole concentration, approximately 92% inhibition of $^3$H-haloperidol binding at 10 n moles concentration, and approximately 100% inhibition of $^3$H-haloperidol binding at 100 n moles concentration in the $^3$H-Haloperidol Receptor Binding Assay.

EXAMPLE 15

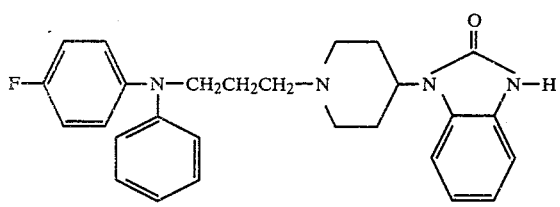

1,3-Dihydro-1-[1-[3-[(4-fluorophenyl)phenylamino]-propyl]-4-piperidinyl]-2H-benzimidazol-2-one 3-[N-phenyl-N-(p-fluorophenyl)]-1-chloropropane is prepared from the reaction of N-phenyl-N-(p-fluorophenyl)amine with 3-chloropropionyl chloride, followed by reduction with borane in tetrahydrofuran, by a procedure analagous to the preparation of 3-[N,N-diphenylamino]-1-bromopropane in Example 2. N-phenyl-N-(p-fluorophenyl)amine is, in turn, prepared according to the procedure disclosed in Lichtenberger et al., *Bull. Soc. Chim. France* 1951: 318–25.

A mixture of 7.0 g. (0.026 moles) of 3-[N-phenyl-N-(p-fluorophenyl)]-1-chloropropane, 5.5 g. (0.026 moles) of 4-(2-keto-1-benzimidazolinyl)piperidine (available from the Aldrich Chemical Company, Milwaukee, Wisconsin), 4.0 g. (0.079 moles) of potassium carbonate, and 1.0 g. of sodium iodide in 50 ml of 4-methyl-2-pentanone is refluxed for about 18 hours. The reaction mixture is cooled and the solvent is evaporated.

Water is then added and the product is extracted into chloroform. The chloroform is evaporated and the residue is twice recrystallized from ethyl acetate-ethanol and once from acetonitrile-ethanol to give 4.3 g. of 1,3-dihydro-1-[1-[3-[(4-fluorophenyl)phenylamino]-propyl]-4-piperidinyl]-2H-benzimidazol-2-one, mp. 171°–172.5° C.

1,3-Dihydro-1-[1-[3-[(4-fluorophenyl)phenylamino]-propyl]-4-piperinyl]-2H-benzimidazol-2-one shows approximately 74% inhibition of $^3$H-haloperidol binding at 10 n moles concentration and approximately 100% inhibition of $^3$H-haloperidol binding at 100 n moles concentration in the $^3$H-Haloperidol Receptor Binding Assay.

EXAMPLE 16

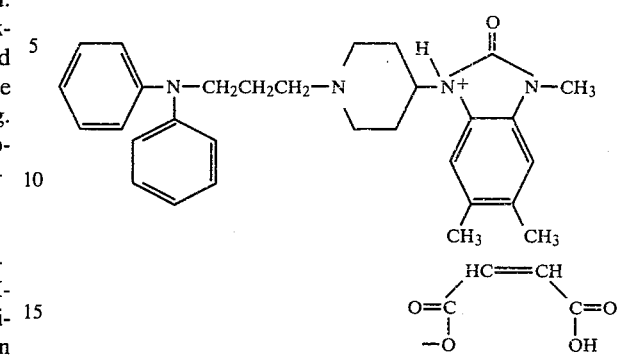

1-[1-([3-Diphenylamino]propyl)-4-piperidinyl]-1,3-dihydro-3,5,6-trimethyl-2H-benzimidazol-2-one butenedioate 1-[4-piperidyl]-3,5,6-trimethylbenzimidazol-2-one is prepared from 1-[1-benzyl-1,2,3,4-tetrahydro-4-piperidyl]-5,6-dimethylbenzimidazol-2-one (preparation described in U.S. Pat. No. 3,161,645 to Janssen, issued Dec. 15, 1964) in a manner similar to the one described for the preparation of 1-(4-piperidyl)-3-methylbenzimidazol-2-one in U.S. Pat. No. 3,161,645.

A mixture of 4.87 g. (0.0165 moles) of 1-(4-piperidyl)-3,5,6-trimethylbenzimidazol-2-one, 5.15 g. (0.0210 moles) of 3-N,N-diphenylamino]-1-chloropropane, 5.0 g. (0.047) moles of sodium carbonate, and 0.5 g. of sodium iodide in 75 ml. of methyl isobutyl ketone is refluxed for about 20 hours. Solvent is evaporated. Water is added to the residue and the product is extracted into chloroform and passed through a column of silica gel. The column is washed with chloroform and the product is then eluted with chloroformethyl acetate. The combined product fractions are evaporated and the residue is dissolved in ethyl ether and converted to the maleate salt with a solution of maleic acid in ethyl ether. Recrystallization from ethanol give 4.2 g. of 1-[1-[(3-diphenylamino)propyl]-4-piperidinyl]-1,3-dihydro-3,5,6-trimethyl-2H-benzimidazol-2-one butenedioate (1:1), mp. 171.0°–172.5° C.

1-[1-[(3-Diphenylamino)propyl]-4-piperidinyl]-1,3-dihydro-3,5,6-trimethyl-2H-benzimidazol-2-one shows approximately 6% inhibition of $^3$H-haloperidol binding at 10 n moles concentration and approximately 60% inhibition of $^3$H-haloperidol binding at 100 n moles concentration in the $^3$H-Haloperidol Receptor Binding Assay.

EXAMPLE 17

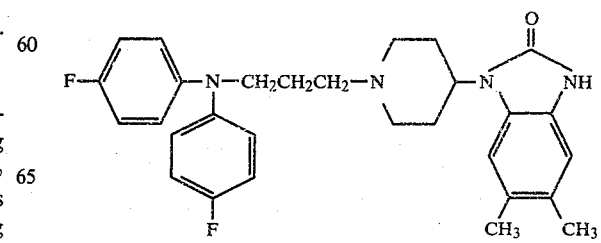

1-[1-[3-[Bis-(4-fluorophenyl)amino]propyl]-4-piperidyl]-1,3-dihydro-5,6-dimethyl-2H-benzimidazol-2-one A mixture of 14.7 g. (0.0600 moles) of 5,6-dimethyl-1,3-dihydro-1-(4-piperidinyl)-b 2H-benzimidazol-2-one (preparation described in Example 39), 16.9 g. (0 .0600 moles) of 3-[N,N-di(4-fluorophenylamino)]-1-chloropropane, 10.6 g. (0.076 moles) of potassium carbonate, and 1.0 g. of sodium chloride in 100 ml. of methyl isobutyl ketone is refluxed for about 16 hours. Solvent is evaporated. Water is added to the residue and the product is extracted into chloroform. The chloroform is evaporated and the residue is recrystallized from acetonitrile and then twice from acetonitrile-chloroform to give 4.2 g. of 1-[1-[3-[bis(4-fluorophenyl)amino]propyl]-4-piperidyl]-1,3-dihydro-5,6-dimethyl-2H-benzimidazol-2-one, mp. 219°–220.5° C.

1-[1-[3-[Bis(4-fluorophenyl)amino]propyl]-4-piperidyl]-1,3-dihydro-5,6-dimethyl-2H-benzimidazol-2one shows approximately 29% inhibition of $^3$H-haloperidol binding at 1 n mole concentration, approximately 85%/76% inhibition of $^3$H-haloperidol binding at 10 n moles concentration, and approximately 100% inhibition of $^3$H-haloperidol binding at 100 n moles concentration in the $^3$H-Haloperidol Receptor Binding Assay.

EXAMPLE 18

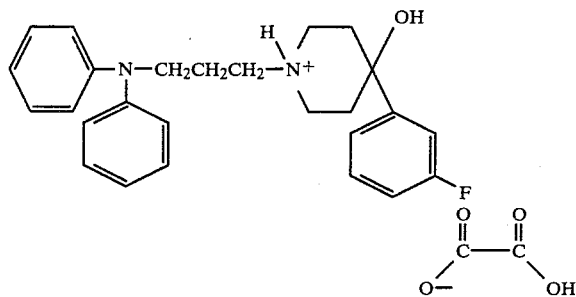

1-[3-(Diphenylamino)propyl]-4-(3-fluorophenyl)-4-piperidinol ethanedioate

A Grignard reagent is prepared in the usual way from 203 g. (1.16 moles) of 3-bromofluorobenzene and 27.8 g. (1.16 moles) of magnesium in 2 l. of ethyl ether. The product is refluxed for 1.5 hours, 220 g. (1.16 moles) of N-benzyl-4-piperidone is gradually added, and the reaction is again refluxed for about 1.5 hours. The resulting complex is then hydrolyzed by adding saturated ammonium chloride. After stirring for 15 minutes, the layers are separated. The ethereal layer is concentrated and the residue crystallized to give 159 g. of 1-benzyl-4-(3-fluorophenyl)-4-piperidinol in three crops.

A 77 g. portion of 1-benzyl-4-(3-fluorophenyl)-4-piperidinol in 500 ml. of methanol is shaken under about 50 psi. of hydrogen for about 8 hours at room temperature in the presence of 3 g. of 20% Pd/C. The reaction is filtered and solvent was evaporated. The residue is dissolved in toluene and filtered. Petroleum ether is added and the resulting crystals filtered to give 43 g. of 4-(3-fluorophenyl)-4-piperidinol, mp. 95°–106° C. A 12 g. portion of this material is recrystallized from toluene and petroleum ether to give 5 g. of the pure product, mp. 118°–120° C.

A mixture of 10.4 g. (0.018 moles) of 3-[N,N-diphenylamino]-1-bromopropane, 3.5 g. (0.018 moles) of 4-(3-fluorophenyl)-4-piperidinol, 1.9 g. (0.018 moles) of sodium carbonate and 1.0 g. of sodium iodide in 100 ml. of methyl ethyl ketone is refluxed for about 3 hours. The reaction is allowed to cool, filtered and the filtrate is evaporated. The residue is shaken with a mixture of diethyl ether and dilute hydrochloric acid. An oily third phase forms which crystallizes on scratching. This material is recrystallized from isopropanol and then from ethanol, and converted back to the free base. The product is then crystallized from isopropanol containing an excess of oxalic acid giving 2.2 g. of 1-[3-(diphenylamino)propyl]-4-(3-fluorophenyl)-4-piperidinol ethanedioate (1:1), mp. 181°–182.5° C.

1-[3-(Diphenylamino)propyl]-4-(3-fluorophenyl)-4-piperidinol ethanedioate shows approximately 23% inhibition of $^3$H-haloperidol binding at 10 n moles concentration and approximately 83% inhibition of $^3$H-haloperidol binding at 100 n moles concentration in the $^3$H-Haloperidol Receptor Binding Assay.

EXAMPLE 19

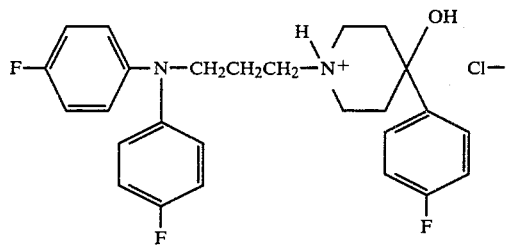

4-(4-Fluorophenyl)-1-(3-[bis(4-fluorophenyl)amino]propyl)-4-piperidinol hydrochloride A mixture of 5.3 g. (0.016 moles) of 3-[N,N-di(p-fluorophenyl)amino]-1-bromopropane, 5.2 g. (0.037 moles) of 1,4-dioxa-8-azaspiro[4,5]decane (available from the Aldrich Chemical Company, Milwaukee, Wis.), and 2.2 g. (0.016 moles) of sodium carbonate in 40 ml. of ethanol is refluxed for about 18 hours. Availability of 1,4-dioxa-8-azaspiro[4,5]decane is also described in British Patent No. 881,893 to Janssen, published Nov. 8, 1961. The reaction mixture is cooled and filtered and the filtrate is evaporated. The residue is taken up in ether and washed with water. The ether is dried and evaporated and the residue is taken up in heptane and filtered free of insolubles. The filtrate is evaporated and the residue is refluxed for about 9 hours in 1 N hydrochloric acid. The reaction mixture is then made basic with aqueous sodium bicarbonate and extracted into methylene chloride. The methylene chloride is evaporated and the residue is taken up in ethyl acetate and chromatographed on a column of silica gel, eluting with ethyl acetate. The combined product fractions are evaporated to give 2.0 g. of 1-(3-[bis(4-fluorophenyl)amino]propyl)-4-piperidone which appears clean by thin layer chromatography.

A mixture of 3.5 g. (0.02 moles) of 4-bromofluorobenzene, 0.49 g. (0.02 moles) of magnesium turnings, and a crystal of iodine in ether is warmed until a reaction begins. The reaction is then refluxed for about ½ hour. A solution of 3.2 g. (0.01 moles) of 1-(3-[bis(4-fluorophenyl)amino]propyl)-4-piperidone in ether is added and the reaction is refluxed about an hour. The reaction is decomposed by the addition of dilute hydrochloric acid. The ether layer is washed with water, dried, and evaporated. The residue is converted to a crystalline hydrochloride salt with HCl in isopropanol and then recrystallized from isopropanol to give about 0.60 g. of 4-(4-fluorophenyl)-1-(3-[bis(4-fluorophenyl)amino]-propyl)-4-piperidinol hydrochloride, mp. 162°–163° C.

4-(4-Fluorophenyl)-1-(3-[bis(4-fluorophenyl)amino]-propyl)-4-piperidinol may also be prepared in accordance with the procedure disclosed in Example 1, by the condensation of 3-[N,N-di(4-fluorophenylamino)]-1-bromopropane with 4-fluorophenyl-4-piperidinol of the formula

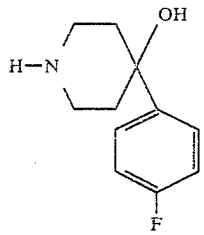

The synthesis of 4-fluorophenyl-4-piperidinol is described in British Patent No. 881,893 to Janssen, published Nov. 8, 1961.

4-(4-Fluorophenyl)-1-(3-[bis(4-fluorophenyl)amino]-propyl)-4-piperidinol hydrochloride shows approximately 25% inhibition of $^3$H-haloperidol binding at 1 n mole concentration and approximately 82% inhibition of $^3$H-haloperidol binding at 10 n moles concentration in the $^3$H-Haloperidol Receptor Binding Assay.

EXAMPLE 20

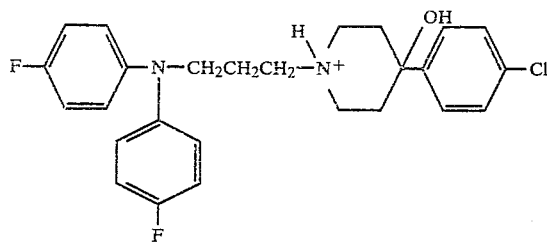

1-(3-[Bis(4-fluorophenyl)amino]propyl)-4-(4-chlorophenyl)-4-piperidinol ethanedioate 3-[N,N-di(4-fluorophenylamino]-1-bromopropane is prepared from the reaction of N,N-di(4-fluorophenyl)amine with 3-chloropropionyl chloride followed by reduction with borane in tetrahydrofuran by a procedure analogous to the preparation of 3-[N,N-diphenylamino]-1-bromopropane in Example 2.

A mixture of 6.65 g. (0.0236 moles) of 3-[N,N-di(4-fluorophenylamino)]-1-bromopropane, 5.0 g. (0.0236 moles) of 4-(p-chlorophenyl)-4-hydroxypiperidine (available from the Aldrich Chemical Company, Milwaukee, Wis.), 3.45 g. (0.025 moles) of potassium carbonate, and 0.5 g. of sodium iodide in 50 ml. of methyl isobutyl ketone is refluxed for about 18 hours. Solvent is evaporated, water is added, and the product is extracted into chloroform. The chloroform solution is dried and evaporated. The residue is recrystallized from isopropyl alcohol to give 3.8 g. of 1-(3-[bis(4-fluorophenyl)amino]propyl)-4-(4-chlorophenyl)-4-piperidinol ethanedioate (1:1), mp. 124°–125° C.

1-(3-[Bis(4-fluorophenyl)amino]propyl)-4-(4-chlorophenyl)-4-piperidinol ethanedioate shows approximately 74% inhibition of $^3$H-haloperidol binding at 10 n moles concentration and approximately 100% inhibition of $^3$H-haloperidol binding at 100 n moles concentration in the $^3$H-Haloperidol Receptor Binding Assay.

EXAMPLE 21

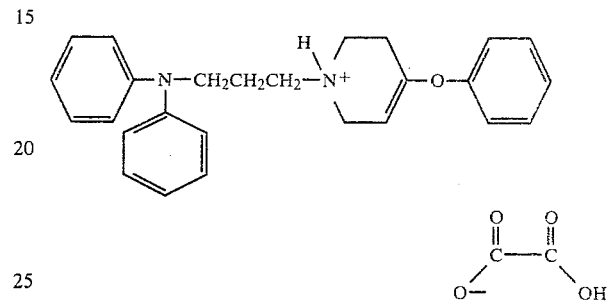

3,6-Dihydro-4-phenoxy-N,N-diphenyl-1(2H)-pyridinepropanamine ethanedioate.

A solution of 3.44 g. of aluminum chloride in 5 ml. of ether is slowly added to a suspension of 3.10 g. of lithium aluminum hydride in 60 ml. of ether. After the mixture has been stirred for about 30 minutes, a solution of 7.50 g. of 4-phenoxypyridine in 50 ml. of ether is cautiously added. The mixture is stirred at room temperature for about 18 hours after which the excess aluminum hydride is destroyed by careful addition of water. The mixture is filtered, and the filtrate is evaporated. Distillation of the residue gives a yellow oil, b.p. 146°–154° C. (12 mm). The hydrochloride salt is formed as a white powder, mp. 143°–145° C.

A mixture of 8.76 g. (0.050 moles) of 4-phenoxy-1,2,3,6-tetrahydropiperidine, 14.5 g. (0.050 moles) of 3-[N,N-diphenylamino]-1-bromopropane, 5.3 g (0.050 moles) of sodium carbonate and 1.0 g. of sodium iodide in 100 ml. of toluene is refluxed for about 16 hours. The reaction mixture is cooled, washed with water, and shaken with dilute hydrochloric acid. The third layer which forms is redissolved into the organic phase by the addition of chloroform. The organic phase is dried, evaporated, redissolved in chloroform, and passed through a column of silica gel eluting with chloroform. The product fractions are combined, evaporated, crystallized from isopropanol containing an excess of oxalic acid, and recrystallized from ethanol to give 11.7 g. of 3,6-dihydro-4-phenoxy-N,N-diphenyl-1(2H)-pyridinepropanamine ethanedioate (1:1), mp. 160°–161° C.

3,6-Dihydro-4-phenoxy-N,N-diphenyl-1(2H)-pyridinepropanamine ethanedioate shows approximately 8% inhibition of $^3$H-haloperidol binding at 10 n moles concentration and approximately 48% inhibition of $^3$H-haloperidol binding at 100 n moles concentration in the $^3$H-Haloperidol Receptor Binding Assay.

EXAMPLE 22

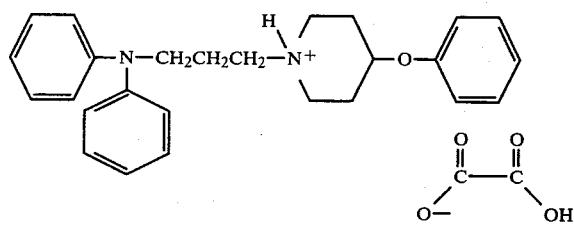

4-Phenoxy-N,N-diphenyl-1-piperidinepropanamine ethanedioate

A mixture of 5.57 g. (0.0117 moles) of 3,6-dihydro-4-phenoxy-N,N-diphenyl-1(2H)-pyridine propanamine ethanedioate (1:1) (preparation described in Example 14), 90 ml. of methanol, 10 ml. of acetic acid and 0.5 g. of 20% Pd/c is shaken under 50 psi. of hydrogen at room temperature for about 4.5 hours. The reaction mixture is then filtered, solvent is evaporated and the residue crystallized from aqueous isopropanol to give 4.3 g. of 4-phenoxy-N,N-diphenyl-1-piperidinepropanamine ethanedioate (1:1), mp. 166°–167.5° C.

4-Phenoxy-N,N-diphenyl-1-piperidinepropanamine may also be prepared in accordance with Example 2, by the condensation of 3-[N,N-diphenylamino]-1-bromopropane with 4-phenoxypiperidine of the formula

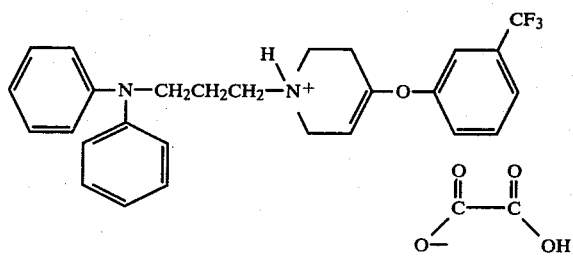

Synthesis of 4-phenoxypiperidine is described in U.S. Pat. No. 3,260,723 to L'Italien and Campbell, issued July 12, 1966.

4-Phenoxy-N,N-diphenyl-1-piperidinepropanamine ethanedioate shows approximately 7% inhibition of $^3$H-haloperidol binding at 10 n moles concentration and approximately 59% inhibition of $^3$H-haloperidol binding at 100 n moles concentration in the $^3$H-Haloperidol Receptor Binding Assay.

EXAMPLE 23

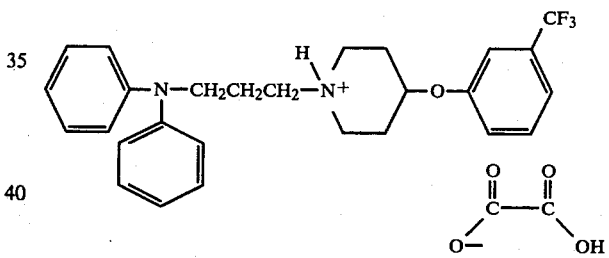

3,6-Dihydro-N,N-diphenyl-4-[(3-trifluoromethyl)-phenoxy]-1(2H)-pyridinepropanamine ethanedioate 4-([3-trifluoromethyl]phenoxy)-1,2,3,6-tetrahydropyridine is prepared by reacting 4-(3-trifluoromethyl)phenoxypyridine (preparation disclosed at D. E. Butler et al., *J. Med. Chem.* 14:575 (1971)), and aluminum hydride in accordance with the procedure outlined for preparing 4-phenoxy-1,2,3,6-tetrahydropyridine in Example 14. Preparation of 4-([3-trifluoromethyl]-phenoxy)-1,2,4,6-tetrahydropyridine is also described in U.S. patent application Ser. No. 922,512 (Wise et al.), filed July 10, 1978.

A mixture of 11.0 g. (0.050 moles) of 4-([3-trifluoromethyl]phenoxy)-1,2,3,6-tetrahydropyridine, 18.6 g. (0.050 moles) of 3-[N,N-diphenylamino]-1-bromopropane hydrobromide, 10.6 g. (0.10 moles) of sodium carbonate and 1.0 g. sodium iodide in 100 ml. toluene is refluxed for about 20 hours. The reaction mixture is cooled and washed with water, dilute hydrochloric acid, dilute caustic, again with water, then dried and evaporated. The residue is taken up in chloroform and passed through a column of silica gel, eluting with chloroform. The combined product fractions are evaporated. The residue is crystallized from isopropanol containing an excess of oxalic acid, and recrystallized from ethanol to give 13.8 g. of 3,6-dihydro-N,N-diphenyl-4-[3-(trifluoromethyl)phenoxy]-1(2H)-pyridinepropanamine ethanedioate (1:1), mp. 148°–149.5° C.

N,N-diphenyl-4-[3-(trifluoromethyl)phenoxy]-1-pyridinepropanamine ethanedioate shows approximately 6% inhibition of $^3$H-haloperidol binding at 10 n moles concentration and approximately 24% inhibition of $^3$H-haloperidol binding at 100 n moles concentration in the $^3$H-Haloperidol Receptor Binding Assay.

EXAMPLE 24

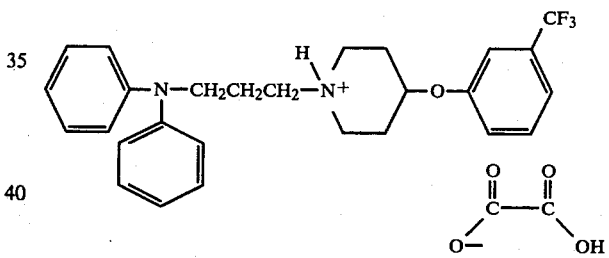

N,N-diphenyl-4-[3-(trifluoromethyl)phenoxy]-1-piperidinepropanamine ethanedioate A mixture of 7.7 g. (0.014 moles) of 3,6-dihydro-N,N-diphenyl-4-[3-(trifluoromethyl)phenoxy]-1(2H)-pyridinepropanamine ethanedioate (1:1) (preparation described in Example 16), 90 ml. of methanol, 10 ml. of acetic acid and 0.5 g. of 20% Pd/c is shaken under 50 psi. of hydrogen at room temperature for about 4 hours. The reaction mixture is then filtered, and the solvent is evaporated. The residue is initially recrystallized from aqueous isopropanol, then recrystallized from aqueous isopropanol, and again recrystallized from aqueous ethanol to give 5.0 g of N,N-diphenyl-4[3-(trifluoromethyl)phenoxyl]-1-piperidinepropanamine ethanedioate (1:1), mp. 189°–190.5° C.

N,N-diphenyl-4-[3-(trifluoromethyl)phenoxy]-1-piperidinepropanamine may also be prepared in accordance with the procedure disclosed in Example 2, by the condensation of 3-[N,N-diphenylamino]-1-bromopropane with 4-[3-(trifluoromethyl)phenoxy]-1-piperidine of the formula

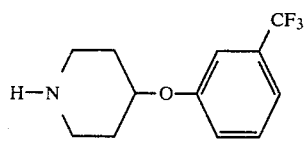

Synthesis of 4-[3-(trifluoromethyl)phenoxy]-1-piperidine is described at R. F. Boswell et al., *J. Med. Chem.* 17: 1000 (1974).

N,N-diphenyl-4-[3-(trifluoromethyl)phenoxy]-1-piperidine shows approximately no inhibition of ³H-haloperidol binding at 10 n moles concentration and approximately 8% inhibition of ³H-haloperidol binding at 100 n moles concentration in the ³H-Haloperidol Receptor Binding Assay.

EXAMPLE 25

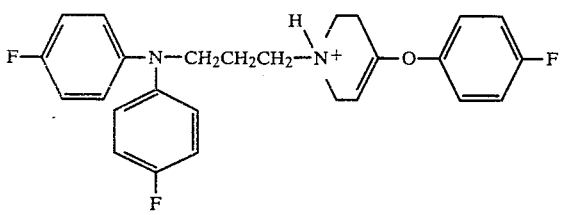

4-(4-Fluorophenoxy)-N,N-bis(4-fluorophenyl)-1,2,3,6-tetrahydro-1-pyridinepropanamine-d-2,3-dihydroxybutanedioate A mixture of 2.7 g. (0.014 moles) of 4-(4-fluorophenoxy)pyridine,(preparation described at D. E. Butler et al., *J. Med. Med.* 14: 575 (1971)), 4.6 g. (0.014 moles) of 3-[N,N-di(p-fluorophenyl)amino]-1-bromopropane and 2.8 g. (0.018 moles) of sodium iodide in 25 ml. of methyl ethyl ketone is refluxed for about 20 hours. The reaction mixture is filtered and the filtrate is evaporated. The residue is triturated with ethyl ether and the resulting crystals filtered and washed with ethyl ether to give 7.1 g. of 4-(4-fluorophenoxy)-1-(3-[bis(4-fluorophenyl)amino]propyl)pyridinium iodide, mp. 147°–148° C.

A mixture of 7.1 g. (0.013 moles) of 4-(4-fluorophenoxy)-1-(3-[bis(4-fluorophenyl)amino]propyl)-pyridinium iodide in methanol is stirred while 0.68 g. (0.0063 moles) of potassium borohydride is added portion-wise over a 5 minute period. Gas is evolved and the temperature rises to a maximum of about 40° C. The reaction is stirred for 90 minutes at ambient temperature following the addition of potassium borohydride. Solvent is evaporated. The residue is dissolved in ethyl ether and washed with water. Solvent is removed. The residue is taken up in a mixture of cyclohexane and carbon tetrachloride and filtered free of some insoluble material. Solvent is again evaporated and the residue is converted to the tartrate salt and chromatographed on a column of silica gel, eluting with acetonitrile. The product fractions are combined. Solvent is evaporated and the residue is triturated with hexane giving about 1.9 g. of 4-(4-fluorophenoxy)-N,N-bis(4-fluorophenyl)-1,2,3,6-tetrahydro-1-pyridinepropanamine-d-2,3-dihydroxybutanedioate (1:1) as an amorphous solid, mp. 67°–77° C.

4-(4-Fluorophenoxy)-N,N-bis(4-fluorophenyl)-1,2,3,6-tetrahydro-1-pyridinepropanamine may also be prepared in accordance with the procedure disclosed in Example 1, by the condensation of 3-[N,N-di(4-fluorophenylamino)]-1-bromopropane with 4-(4-fluorophenoxy)-1,2,3,6-tetrahydropyridine of the formula

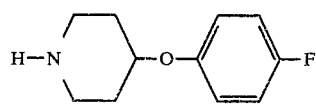

Synthesis of 4-(4-fluorophenoxy)-1,2,3,6-tetrahydropyridine is described in U.S. Pat. No. 3,260,723 to L'Italien and Campbell, issued July 12, 1966.

4-(4-Fluorophenyl)-N,N-bis(4-fluorophenyl)-1,2,3,6-tetrahydro-1-pyridinepropanamine-d-2,3-dihydroxybutanedioate shows approximately no inhibition of ³H-haloperidol binding at 1 n mole concentration and approximately 43% inhibition of ³H-haloperidol binding at 10 n moles concentration in the ³H-Haloperidol Receptor Binding Assay.

EXAMPLE 26

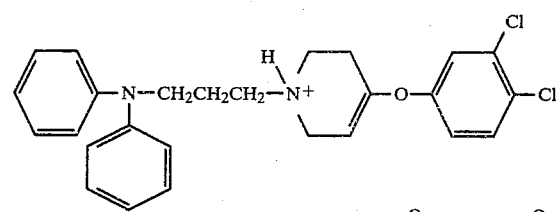

4-(3,4-Dichlorophenoxy)-3,6-dihydro-N,N-diphenyl-1(2H)-pyridinepropanamine ethanedioate 4-(3,4-Dichlorophenoxy)-1,2,3,6-tetrahydropyridine is prepared by reacting 4-(3,4-dichlorophenoxy)pyridine (availability described in U.S. Pat. No. 3,429,689 to Duerr et al., issued Feb. 25, 1969), with aluminum hydride in accordance with the procedure outlined for preparing 4-phenoxy-1,2,3,6-tetrahydropyridine in Example 14. Preparation of 4-(3,4-dichlorophenoxy)-1,2,3,6-tetrahydropyridine is described in U.S. Patent application Ser. No. 922,512 (Wise et al.), filed July 10, 1978.

A mixture of 11.0 g. (0.050 moles) of 4-(3,4-dichlorophenoxy)-1,2,3,6-tetrahydropyridine, 18.6 g. (0.050 moles) of 3-[N,N-diphenylamino]-1-bromopropane hydrobromide, 10.6 g. of sodium carbonate and 1.0 g. of sodium iodide in 100 ml. of toluene is refluxed for about 20 hours. The reaction is cooled, washed with water, dilute hydrochloric acid, then with dilute caustic. The toluene solution is dried and solvent is evaporated. The residue is dissolved in chloroform and chromatographed on a column of silica gel, eluting with chloroform. The combined product fractions are evaporated, crystallized from isopropanol containing an excess of oxalic acid, and recrystallized from ethanol to give 10.4 g. of 4-(3,4-dichlorophenoxy)-3,6-dihydro-N,N-diphenyl-1(2H)-pyridinepropanamine ethanedioate (1:1), mp. 170.5°–171.5° C.

4-(3,4-Dichlorophenoxy)-3,6-dihydro-N,N-diphenyl-1(2H)-pyridinepropanamine shows approximately no inhibition of $^3$H-haloperidol binding at 10 n moles concentration, and approximately 26% inhibition of $^3$H-haloperidol binding at 100 n moles concentration in the $^3$H-Haloperidol Receptor Binding Assay.

EXAMPLE 27

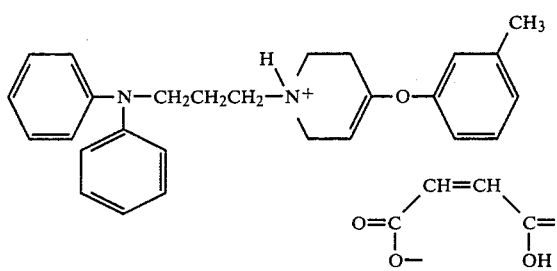

3,6-Dihydro-4-(3-methylphenoxy)-N,N-diphenyl-1(2H)-pyridinepropanamine butenedioate A mixture of 8.0 g. (0.032 moles) of 3-(N,N-diphenylamino)-1-chloropropane, 6.0 g. (0.032 mles) of 4-(3-methylphenoxy)pyridine (preparation described at D. E. Butler et al, J. Med. Chem. 14: 575 (1971)), 4.9 g. (0.030 moles) of potassium iodide and 60 ml. of methyl ethyl ketone are refluxed for about 72 hours.

The reaction mixture is cooled, filtered and the filtrate is evaporated. The residue yields approximately 13 g. of 4-(3-methylphenoxy)-1-(3-[diphenylamino]-propyl)pyridinium iodide.

5.0 g. of sodium borohydride, (0.131 moles) is added portionwise to a solution of 13 g. (0.032 moles) of 4-(3-methylphenoxy)-1-[3-(N,N-diphenylamino)propyl]-pyridinium iodide in 200 ml. of methanol over a 10 minute period, allowing the temperature to reach reflux. The reaction is refluxed another 20 minutes. Solvent is evaporated. The residue is dissolved in chloroform, washed with sodium carbonate solution, and dried. Solvent is evaporated. The residue is converted to the maleate in ether and recrystallized from acetonitrile to give 10.9 g. of 3,5-dihydro-4-(3-methylphenoxy)-N,N-diphenyl-1(2H)- pyridinepropanamine butenedioate (1:1), mp. 164°–166° C.

3,5-Dihydro-4-(3-methylphenoxy)-N,N-diphenyl-1(2H)-pyridinepropanamine may also be prepared in accordance with the procedure disclosed in Example 2, by the condensation of 3-[N,N-diphenylamino]-1-bromopropane with 4-(3-methylphenoxy)-1,2,3,6-tetrahydropyridine of the formula

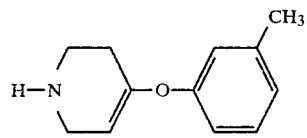

Synthesis of 4-(3-methylphenoxy)-1,2,3,6-tetrahydropyridine is described in U.S. patent application Ser. No. 922,512 (Wise et al.), filed July 10, 1978.

EXAMPLE 28

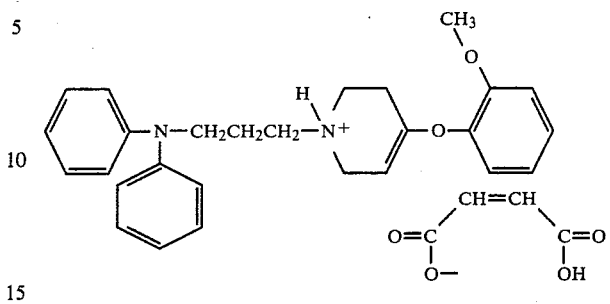

3,6-Dihydro-4-(2-methoxyphenoxy)-N,N-diphenyl-1(2H)-pyridine-propanamine butenedioate In accordance with the procedure outlined for preparing 4-(3-methylphenoxy)-1-(3-[diphenylamino]-propyl)pyridinium iodide in Example 20, 4-(2-methoxyphenoxy)-1-(3-[diphenylamino]propyl)-pyridinium iodide is prepared from 3-(N,N-diphenylamino)-1-chloropropane and 4-(2-methoxyphenoxy)pyridine (preparation described at D. E. Butler et al., J. Med. Chem. 14: 575 (1971)).

5.0 g. of sodium borohydride (0.131 moles) is added portionwise to a solution of 13 g. (0.030 moles) of 4-(2-methoxyphenoxy)-1-[3-(N,N-diphenylamino)propyl]-pyridinium iodide in 200 ml. of methanol over a 10 minute period, allowing the temperature to reach reflux. The reaction is refluxed another 15 minutes. Solvent is evaporated. The residue is dissolved in chloroform, washed with sodium carbonate solution and dried. Solvent is evaporated. The residue is converted to the maleate in ether and then recrystallized twice from ethyl acetate-acetonitrile to give 2.1 g. of 3,6-dihydro-4-(2-methoxyphenoxy)-N,N-diphenyl-1-(2H)-pyridinepropanamine butenedioate, mp. 155.5°–157.5° C.

3,6-Dihydro-4-(2-methoxyphenoxy)-N,N-diphenyl-1(2H)-pyridinepropanamine may also be prepared in accordance with the process disclosed in Example 2, by the condensation of 3-[N,N-diphenylamino]-1-bromopropane with 4-(2-methoxyphenoxy)-1,2,3,6-tetrahydropyridine of the formula

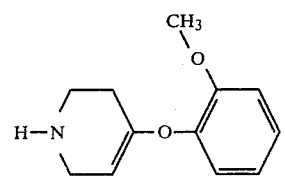

Synthesis of 4-(2-methoxyphenoxy)-1,2,3,6-tetrahydropyridine is described in U.S. patent application Ser. No. 922,512 (Wise et al.), filed July 10, 1978.

EXAMPLE 29

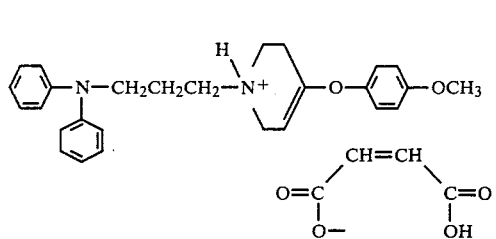

3,6-Dihydro-4-(4-methoxyphenoxy)-N,N-diphenyl-1(2H)-pyridinepropanamine butenedioate In accordance with the procedure outlined for preparing 4-(3-methylphenoxy)-1-(3-[diphenylamino]propyl)pyridinium iodide in Example 20, 4-(4-methoxyphenoxy)-1-(3-[diphenylamino]propyl)pyridinium iodide is prepared from 3-(N,N-diphenylamino)-1-chloropropane and 4-(4-methoxyphenoxy)pyridine (preparation disclosed at D. E. Butler et al., *J. Med. Chem.* 14: 575 (1971)).

5.0 g. of sodium borohydride (0.131 moles) is added portionwise to a solution of 11 g. (0.025 moles) of 4-(4-methoxyphenoxy)-1-[3-(N,N-diphenylamino)propyl]-pyridinium iodide in 200 ml. of methanol over a 10 minute period, allowing the temperature to reach reflux. The reaction is refluxed another 15 minutes. Solvent is evaporated. The residue is dissolved in chloroform, washed with sodium carbonate solution and dried. The residue is converted to the maleate salt in ether, recrystallized from acetonitrile and recrystallized again from acetonitrile-ethyl acetate to give 5.15 g. of 3,6-dihydro-4-(4-methoxyphenoxy)-N,N-diphenyl-1-(2H)-pyridinepropanamine butenedioate, (1:1) mp. 140°–142° C.

3,6-Dihydro-4-(4-methoxyphenoxy)-N,N-diphenyl-1(2H)-pyridinepropanamine may also be prepared in accordance with the procedure disclosed in Example 2, by the condensation of 3-[N,N-diphenylamino]-1-bromopropane with 4-(4-methoxyphenoxy)-1,2,3,6-tetrahydropyridine of the formula

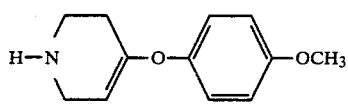

Synthesis of 4-(4-methoxyphenoxy)-1,2,3,6-tetrahydropyridine may be accomplished by a procedure analogous to the synthesis of 4-(2-methoxyphenoxy)-1,2,3,6-tetrahydropyridine in U.S. patent application Ser. No. 922,512 (Wise et al.), filed July 10, 1978.

EXAMPLE 30

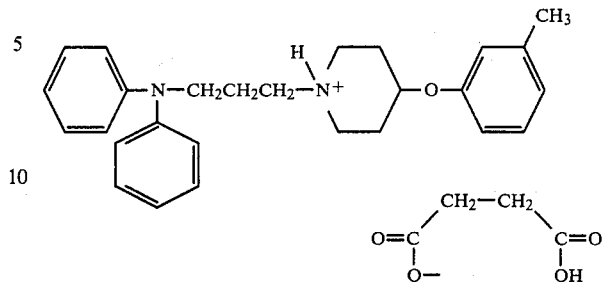

N,N-diphenyl-4-[3-methylphenoxy]-1-piperidine-propanamine butanedioate

A mixture of 4.29 g. (0.00833 moles) of 3,6-dihydro-4-(3-methylphenoxy)-N,N-diphenyl-1(2H)-pyridinepropanamine butanedioate (1:1) (preparation of the butenedioate salt described in Example 20), 0.5 g. of 20% Pd/C in 50 ml. of dimethylformamide (DMF), and 50 ml. of methanol is hydrogenated at room temperature under about 50 psi. of hydrogen for about 4 hours. The reaction mixture is filtered, solvent is evaporated, and the residue chromatographed on a column of silica gel, eluting the product with ethyl acetate. The combined product fractions are concentrated and crystallized from ether to give 0.3 g. of N,N-diphenyl-4-[3-methylphenoxy]-1-piperidinepropanamine butanedioate (1:1), mp. 119°–121° C.

N,N-diphenyl-4-[3-methylphenoxy]-1-piperidinepropanamine may also be prepared in accordance with the procedure disclosed in Example 2, by the condensation of 3-[N,N-diphenylamino]-1-bromopropane with 4-(3-methoxyphenoxy)piperidine of the formula

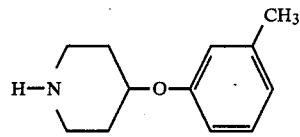

Synthesis of 4-(3-methylphenoxy)piperidine is described in U.S. Pat. No. 4,031,221 to Helsley et al., issued June 21, 1977.

Alternatively, a mixture of 13 g. (0.032 moles) of 4-(3-methylphenoxy)-1-[3-(N,N-diphenyl)amino]propane pyridinium iodide, (see Example 20), 1.0 g. of 20% palladium on carbon and 200 ml. of methanol is shaken in an autoclave at room temperature under 50 psi. of hydrogen until hydrogen uptake is completed. The reaction is then filtered, solvent is evaporated, and the residue is purified to give N,N-diphenyl-4-[3-methylphenoxy]-1-piperidinepropanamine hydriodide.

EXAMPLE 31

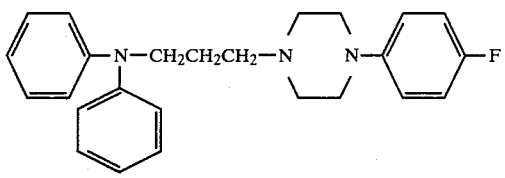

4-(4-Fluorophenyl)-N,N-diphenyl-1-piperazine-
propanamine

A mixture of 13.4 g. (0.023 moles) of 3-[(N,N-diphenylamino]-1-bromopropane, 5.0 g. (0.023 moles) of 1-(4-fluorophenyl)piperazine hydrochloride (available from the Aldrich Chemical Company, Milwaukee, Wis.), 4.9 g. (0.045 moles) of sodium carbonate and 1.0 g. of sodium iodide in 100 ml. of methyl ethyl ketone is refluxed for about 3 hours. The reaction mixture is filtered and evaporated. The residue is shaken with ethyl ether and 1 N hydrochloric acid. The resulting crystals are filtered and recrystallized once from isopropanol and three times from ethanol, reconverted to free base, and recrystallized as the free base from aqueous ethanol to give 3.7 g. of 4-(4-fluorophenyl)N,N-diphenyl-1-piperazinepropanamine, mp. 87°–88° C.

4-(4-Fluorophenyl)-N,N-diphenyl-1-piperazine-propanamine shows approximately no inhibition of $^3$H-Haloperidol binding at 10 n moles concentration and approximately 12% inhibition of $^3$H-haloperidol binding at 100 n moles concentration in the $^3$H-Haloperidol Receptor Binding Assay.

EXAMPLE 32

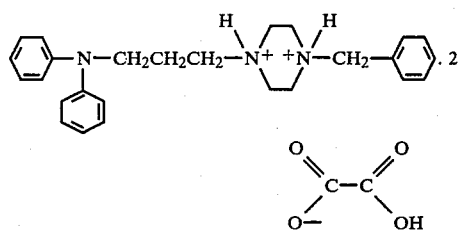

N,N-diphenyl-4-(phenylmethyl)-1-piperazinepropanamine ethanedioate

A mixture of 9.0 g. (0.016 moles) of 3-[N,N-diphenylamino]-1-bromopropane, 4.0 g. (0.016 moles) of 1-benzylpiperazine hydrobromide (available from the Aldrich Chemical Company, Milwaukee, WI), 3.30 g. (0.031 moles) of sodium carbonate and 1.0 g. of sodium iodide in methyl ethyl ketone is refluxed for three hours. The reaction mixture is then filtered and evaporated and the residue is shaken with ethyl ether and 1 N (one normal) hydrochloric acid. The resulting crystals are filtered and recrystallized once from isopropanol and twice from ethanol, converted back to free base, and crystallized from isopropanol containing an excess of oxalic acid. The resulting crystals are finally recrystallized from aqueous ethanol to give 1.2 g. of N,N-diphenyl-4-(phenylmethyl)-1-piperazinepropanamine ethanedioate (1:2), mp. 241°–243° C.

N,N-diphenyl-4-(phenylmethyl)-1-piperazine-propanamine shows approximately 16% inhibition of $^3$H-haloperidol binding at 10 n moles concentration and approximately 33% inhibition of $^3$H-haloperidol binding at 100 n moles concentration in the $^3$H-Haloperidol Receptor Binding Assay.

EXAMPLE 33

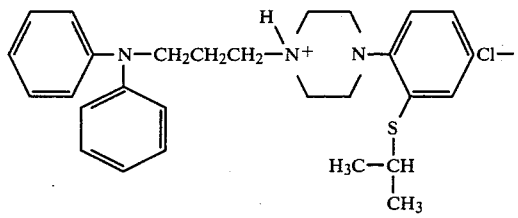

4-[2-[(1-Methylethyl)thio]phenyl]-N,N-diphenyl-1-piperazinepropanamine hydrochloride A mixture of 9.1 g (0.016 moles) of 3-[N,N-diphenylamino]-1-bromopropane, 5.0 g. (0.016 moles) of 1-[2-[(1-methylethyl)-thio]phenyl]piperazine hydrobromide (preparation of the free base described in U.S. Pat. No. 3,007,928 to Robert F. Parcell, issued Nov. 7, 1961), 3.3 g. (0.032 moles) of sodium carbonate, and 1.0 g. of sodium iodide in 100 ml. of methyl ethyl ketone is refluxed for about three hours. The reaction mixture is then filtered and evaporated and the residue is shaken with ethyl ether and 1 N hydrochloric acid. The resulting crystals are filtered and recrystallized from isopropanol and then from ethanol to give 4.0 g. of 4-[2-[(1-methylethyl)thio]phenyl]-N,N-diphenyl-1-piperazinepropanamine monohydrochloride, mp. 189°–190° C.

4-[2-[(1-Methylethyl)thio]phenyl]-N,N-diphenyl-1-piperazinepropanamine hydrochloride shows approximately no inhibition of $^3$H-haloperidol binding at 10 n moles concentration and approximately 28% inhibition of $^3$H-haloperidol binding at 100 n moles concentration in the $^3$H-Haloperidol Receptor Binding Assay.

EXAMPLE 34

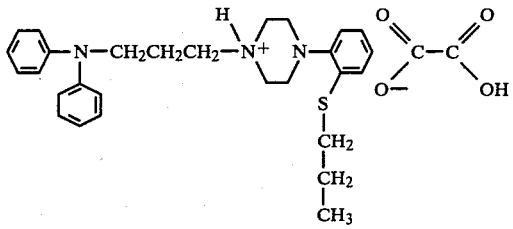

N,N-diphenyl-4-[2-(propylthio)phenyl]-1-piperazinepropanamine ethanedioate

A mixture of 6.54 g. (0.0266 moles) of 3-[N,N-diphenylamino]-1-chloropropane, 6.60 g. (0.0242 moles) of 1-[o-(propylthio)-phenyl]piperazine monohydrochloride (prepared in an analogous manner to the procedure disclosed in U.S. Pat. No. 3,007,928 to Robert F. Parcell, issued Nov. 7, 1961), 5.13 g. (0.0484 moles) of sodium carbonate and 0.5 g. of sodium iodide in 75 ml. of toluene is refluxed for about 20 hours. The reaction mixture is cooled, washed first with water, then with dilute hydrochloric acid, then with dilute caustic and again with water. The toluene solution is dried, solvent is evaporated and the residue is converted to the oxalate salt in isopropyl alcohol. The resulting crystals are filtered and recrystallized from isopropyl alcohol to give 6.80 g. of N,N-diphenyl-4-[2-(propylthio)phenyl]-1-piperazinepropanamine ethanedioate (1:1), mp. 165.5°–167.0° C.

N,N-diphenyl-4-[2-(propylthio)phenyl]-1-piperazine-propanamine shows approximately 6% inhibition of ³H-haloperidol binding at 10 n moles concentration and approximately 64% inhibition of ³H-haloperidol binding at 100 n moles concentration in the ³H-Haloperidol Receptor Binding Assay.

EXAMPLE 35

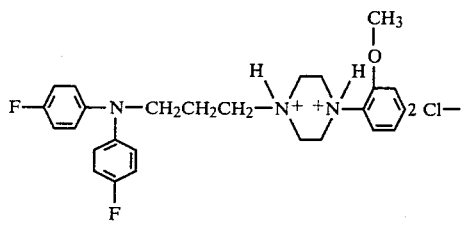

N,N-bis(4-fluorophenyl)-4-(2-methoxyphenyl)-1-piperazinepropanamine dihydrochloride A mixture of 8.0 g. (0.024 moles) of 3-[N,N-diphenylamino]-1-bromopropane, 9.4 g. (0.049 moles) of 1-(2-methoxyphenyl)-piperazine (available from the Aldrich Chemical Company, Milwaukee, WI) and 3.1 g. of sodium iodide in 100 ml of methyl ethyl ketone is refluxed for about 16 hours, cooled and filtered. The filtrate is evaporated and the residue is dissolved in ethyl acetate and chromatographed on a column of silica gel, eluting with ethyl acetate. The product fractions are combined and evaporated and the residue is crystallized from dilute hydrochloric acid to give 5.1 g. of N,N-bis(4-fluorophenyl)-4-(2-methoxyphenyl)-1-piperazinepropanamine dihydrochloride, mp. 224°–226° C.

N,N-bis(4-fluorophenyl)-4-(2-methoxyphenyl)-1-piperazinepropanamine dihydrochloride shows approximately 28% inhibition of ³H-haloperidol binding at 10 n moles concentration and approximately 79% inhibition of ³H-haloperidol binding at 100 n moles concentration in the ³H-Haloperidol Receptor Binding Assay.

EXAMPLE 36

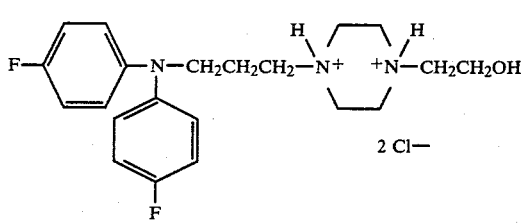

4-[3-[Bis(4-fluorophenyl)amino]propyl]-1-piperazineethanol dihydrochloride

A mixture of 11.5 g. (0.035 moles) of 3-[N,N-di(4-fluorophenylamino)]-1-bromopropane, 9.1 g. (0.070 moles) of N-piperazineethanol (available from the Aldrich Chemical Company, Milwaukee, WI) and 4.5 g. of sodium iodide in 100 ml. of methyl ethyl ketone is refluxed for about 16 hours, cooled and partitioned between ethyl ether and water. The ethereal layer is extracted with 1 N (one normal) hydrochloric acid. The aqueous layer is made basic and extracted into ether. The ethereal layer is evaporated. The residue is crystallized as the hydrochloride salt with hydrochloric acid in isopropanol, and recrystallized from ethanol to give 7.8 g. of 4-[3-bis-(4-fluorophenyl)amino]propyl]-1-piperazineethanol dihydrochloride, mp. 231°–232° C.

4-[3-[Bis(4-fluorophenyl)amino]propyl]-1-piperazine ethanol dihydrochloride shows approximately 21% inhibition of ³H-haloperidol binding at 10 n moles concentration and approximately 62% inhibition of ³H-haloperidol binding at 100 n moles concentration in the ³H-Haloperidol Receptor Binding Assay.

EXAMPLE 37

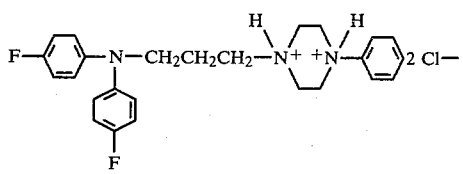

N,N-bis(4-fluorophenyl)-4-phenyl-1-piperazinepropanamine dihydrochloride

A mixture of 8.0 g. (0.024 moles) of 3-[N,N-di(4-fluorophenylamino)]-1-bromopropane, 7.9 g. (0.049 moles) of 1-phenyl-piperazine (available from the Aldrich Chemical Company, Milwaukee, WI) and 3.1 g. of sodium iodide in 80 ml. of methyl ethyl ketone is refluxed for about 16 hours, cooled and filtered. Solvent is evaporated and the residue is dissolved in chloroform, washed with dilute hydrochloric acid, and concentrated to give two crops of crystals. These crystals are recombined and recrystallized from isopropanol to give 2.8 g. of N,N-bis(4-fluorophenyl)4-phenyl-1-piperazinepropanamine dihydrochloride, mp. 205°–210° C.

N,N-bis(4-fluorophenyl)-4-phenyl-1-piperazinepropanamine dihydrochloride shows approximately no inhibition of ³H-haloperidol binding at 10 n moles concentration and approximately 37% inhibition of ³H-haloperidol binding at 100 n moles concentration in the ³H-Haloperidol Receptor Binding Assay.

EXAMPLE 38

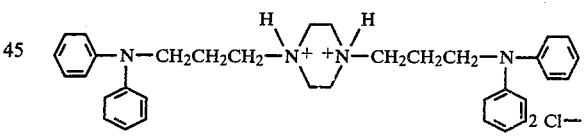

N,N,N',N'-tetraphenyl-1,4-piperazinedipropanamine dihydrochloride 3-(N,N-diphenylamino)-1-chloropropane is prepared by the reaction of diphenylamine with 3-chloropropionyl chloride, followed by reduction with borane in tetrahydrofuran, by a procedure analogous to the preparation of 3-[N,N-diphenylamino]-1-bromopropane in Example 2.

A mixture of 7.37 g. (0.030 moles) of 3-(N,N-diphenylamino)-1-chloropropane, 2.58 g. (0.030 moles) of piperazine (available from the Aldrich Chemical Company, Milwaukee, WI), 7.0 g. (0.066 moles) of sodium carbonate and 0.2 g. of sodium iodide in 50 ml. of toluene is refluxed for about 16 hours. The reaction mixture is cooled, washed with water, and shaken with dilute hydrochloric acid. The resulting white precipitate is filtered and recrystallized from aqueous ethanol and then from water to give 1.0 g. of N,N,N',N'-tetraphenyl-1,4-piperazinedipropanamine dihydrochloride, mp. 273°–277° C.

EXAMPLE 39

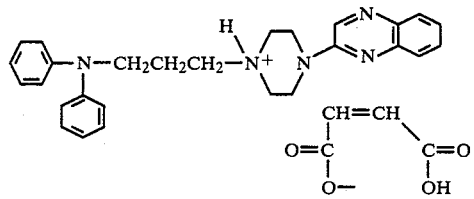

N,N-diphenyl-4-(2-quinoxalinyl)-1-piperazinepropanamine butenedioate 2-(1-Piperazinyl)quinoxaline is prepared from 2-chloroquinoxaline by reaction with piperazine in a manner similar to the preparation of 2-(1-piperazinyl)-quinoxalines described in British Pat. No. 1,440,722, issued June 23, 1976 and assigned to Merck & Co. The preparation of 2-chloroquinoxaline is described at Gowenlock et al., J. Chem Soc. 1945: 622.

A mixture of 3.9 g. (0.018 moles) of 2-(1-piperazinyl)-quinoxaline, 5.4 g. (0.022 moles) of 3-[N,N-diphenylamino]-1-chloropropane, 2.7 g. (0.025 moles) of sodium carbonate, and 3.0 g. of potassium iodide in 50 ml. of n-butanol is refluxed for about 16 hours. The solvent is evaporated. Water is added to the residue and the product is extracted into chloroform. The chloroform is evaporated and the residue is dissolved in ethanol. The product is converted to the hydrochloride salt with aqueous hydrochloric acid. The resulting precipitate is recrystallized three times from ethanol, reconverted to the base, and then to the maleate salt in ether to give 3.7 g. of N,N-diphenyl-4-(2-quinoxalinyl)-1-piperazinepropanamine butenedioate (1:1), mp. 186°–188° C.

EXAMPLE 40

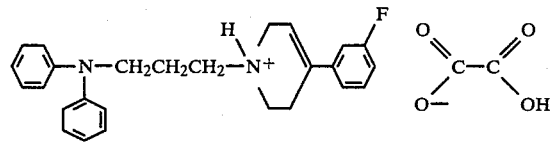

4-(3-Fluorophenyl)-1,2,3,6-tetrahydro-N,N-diphenyl-1-pyridinepropanamine ethanedioate A solution of 87 g. (0.077 moles) of 4-(3-fluorophenyl)-4-piperidinol (preparation described in Example 12) in 90 ml. of toluene is combined with a solution of 16 g. (0.0847 moles) of p-toluenesulfonic acid in 60 ml. of tetrachloroethane. The resulting mixture is refluxed for about 88 hours using a Dean Starke Trap to remove water. The reaction mixture is chilled and filtered. The filter cake is dissolved in hot water and the resulting solution is made basic with caustic, chilled and then filtered. The filter cake is dried, converted to the hydrochloride salt in ethyl ether, combined with a second crop, and recrystallized from isopropanol to give 5.5 g. of 4-(3-fluorophenyl)-1,2,3,6-tetrahydropyridinepropanamine hydrochloride, mp. 182°–184° C.

A mixture of 7.3 g. (0.013 moles) of 3-[N,N-diphenylaminopropyl]-1-bromopropane, 2.7 g. (0.013 moles) of 4-(3-fluorophenyl)-1,2,3,6-tetrahydropyridine hydrochloride, 2.7 g. (0.025 moles) of sodium carbonate, and 1.0 g. of sodium iodide in 100 ml. of methyl ethyl ketone is refluxed for about 3 hours. The reaction is then filtered and the solvent evaporated. The residue is shaken with diethyl ether and 1 N hydrochloric acid. The oily third layer which forms is isolated, then an excess of a solution of aqueous oxalic acid is added. A semi-crystalline gum results which is triturated with acetone to give 1.75 g. of crystalline 4-(3-fluorophenyl)-1,2,3,6-tetrahydro-N,N-diphenyl-1-pyridinepropanamine ethanedioate (1:1), mp. 197°–198.5° C.

4-(3-Fluorophenyl)-2,3,4,6-tetrahydro-N,N-diphenyl-1-pyridinepropanamine ethanedioate shows approximately no inhibition of $^3$H-haloperidol binding at 10 n moles concentration and approximately 23% inhibition of $^3$H-haloperidol binding at 100 n moles concentration in the $^3$H-Haloperidol Receptor Binding Assay.

EXAMPLE 41

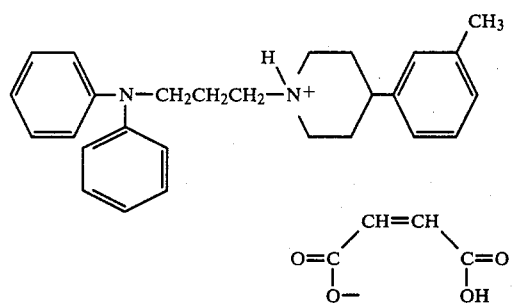

N,N-diphenyl-4-[3-methylphenyl]-1-piperidinepropanamine butenedioate 106 g. of 3-bromotoluene (0.62 moles) in ethyl ether is reacted with 9 g. (1.3 moles) of lithium. When the reaction is complete, 100 g. (0.58 moles) of N-benzyl-4-piperidone (available from the Aldrich Chemical Company, Milwaukee, WI) is added over a 20 minute period. The reaction is then stirred for about 30 minutes. About 500 ml. of water is then cautiously added. The ether layer is isolated, dried and evaporated. The residue is then refluxed in 350 ml. of acetic anhydride for a period of about 5 hours. The reaction product is evaporated under reduced pressure and the oily residue is poured into aqueous caustic with cooling, then extracted into ether. The ether layer is dried and evaporated. The residue is dissolved in 400 ml. of acetic acid and hydrogenated over Pd/c at about 50° C. The product is filtered, evaporated, and the residue distilled to give 61 g. of the free base. This is converted to the hydrochloride salt and recrystallized from isopropanol to give 18 g. of 4-(3-methylphenyl)piperidine hydrochloride, mp. 224°–225° C.

A mixture of 7.37 g. (0.030 moles) of 3-[N,N-diphenylamino]-1-chloropropane, 6.0 g. (0.024 moles) of 4-(3-methylphenyl)-piperidine hydrochloride, 3.92 g. (0.024 moles) of potassium iodide, and 5.30 g. (0.050 moles) of sodium carbonate in 60 ml. of n-butanol is refluxed for about 16 hours. Solvent is evaporated and the residue is dissolved in chloroform and washed with water. The chloroform solution is dried and passed through a column of silica gel. The product is eluted with acetonitrile. The product fractions are combined, concentrated, and converted to the maleate salt in ether. The resulting crystals recrystallized from acetonitrile to give 7.2 g. of N,N-diphenyl-4-[3-methylphenyl]-1-piperidinepropanamine butenedioate (1:1), mp. 137.5°–139.5° C.

N,N-Diphenyl-4-[3-methylphenyl]-1-piperidinepropanamine butenedioate shows approximately 25% inhibition of ³H-haloperidol binding at 10 n moles concentration and approximately 84% inhibition of ³H-haloperidol binding at 100 n moles concentration in the ³H-Haloperidol Receptor Binding Assay.

EXAMPLE 42

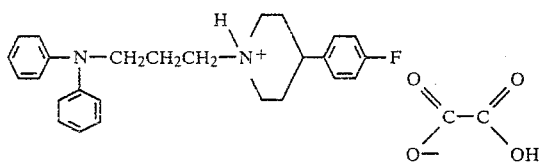

4-[(4-Fluorophenyl)amino]-N,N-diphenyl-1-piperidinepropanamine ethanedioate

A mixture of 5.1 g. (0.021 moles) of 3-[N,N,-diphenylamino]-1-chloropropane, 2.0 g. (0.010 moles) of 4-(4-fluorophenylamino)-piperidine (preparation described in U.S. Pat. No. 3,691,176 to Hallas et al., issued Sept. 12, 1972), 2.2 g. (0.021 moles) of sodium carbonate, and 0.3 g. of sodium iodide in 60 ml. of toluene is refluxed for about 18 hours. The reaction mixture is cooled, washed with water, dried over anhydrous sodium sulfate, and passed through a column of silica gel. Excess chloro compound is eluted with toluene and the product is then eluted with ethyl acetate. The product fractions are combined and solvent is evaporated. The residue is converted to the dioxalate salt in ethanol and then recrystallized from ethanol to give 1.3 g. of 4-[(4-fluorophenyl)amino]-N,N-diphenyl-1-piperidinepropanamine ethanedioate (1:1), mp. 198.5°–200° C. 4-[(4-Fluorophenyl)amino]-N,N-diphenyl-1-piperidinepropanamine shows approximately 26% inhibition of ³H-haloperidol binding at 10 n moles concentration and approximately 90% inhibition of ³H-haloperidol binding at 100 n moles concentration in the ³H-Haloperidol Receptor Binding Assay.

EXAMPLE 43

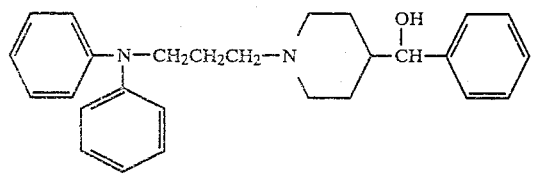

1-[3-(Diphenylamino)propyl]-alpha-phenyl-4-piperidine methanol.

A mixture of 9.8 g. (0.040 moles) of 3-[N,N-diphenylamino]-1-chloropropane, 5.7 g. (0.030 moles) of alpha-phenyl-4-piperidine methanol (preparation described in U.S. Pat. No. 3,029,244 to Lyle, Jr. et al, issued Apr. 10, 1962), 4.2 g. (0.040 moles) of sodium carbonate and 0.5 g. of sodium iodide in 90 ml. of toluene is refluxed for about 18 hours. The reaction mixture is cooled, washed with water, and then shaken with dilute hydrochloric acid. The viscous third layer which falls to the bottom is isolated and shaken with ether and dilute caustic. The resulting ether layer is then washed with water, dried, and passed into a column of silica gel. The product is eluted with ethyl acetate and the product fractions are combined, evaporated, and triturated with isopropyl ether. The resulting crystals are isolated by filtration and recrystallized from ethanol to give 2.0 g of 1-[3-(diphenylamino)propyl]-alpha-penyl-4-piperidine methanol, mp. 129.0°–130.5° C. 1-[3-(Diphenylamino)propyl]-alpha-phenyl-4-piperidine methanol shows approximately no inhibition of ³H-haloperidol binding at 10 n moles concentration and approximately 18% inhibition of hu 3H-haloperidol binding at 100 n moles concentration in the ³H-Haloperidol Receptor Binding Assay.

EXAMPLE 44

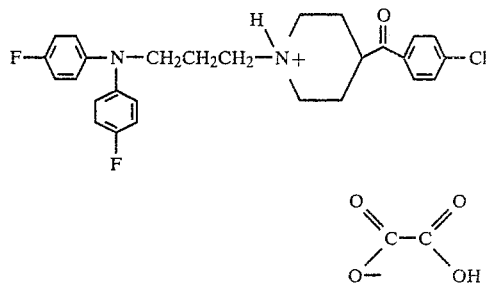

[1-[3-[Bis(4-fluorophenyl)amino]propyl]-4-piperidinyl]-(4-chlorophenyl)methanone ethanedioate A mixture of 11.5 g. (0.035 moles) of 3-[N,N-di(4-fluorophenylamino)]1-bromopropane, 18.2 g. (0.070) moles of 4-piperidinyl-(4-chlorophenyl)methanone hydrochloride (preparation described at Farmaco Ed. Sci. 12: 853 (1958)), 17.3 g. (0.125 moles) of sodium carbonate and 4.5 g of sodium iodide in 100 ml. of methyl ethyl ketone is refluxed for about 16 hours. The reaction mixture is cooled and filtered and the filtrate is evaporated. The residue is crystallized from aqueous ethanol containing an excess of oxalic acid and then recrystallized from methanol to give 9.8 g. of [1-[3-[bis(4-fluorophenyl)amino]propyl]-4-piperidinyl]-(4-chlorophenyl)methanone ethanedioate (1:1), mp. 201.5°–203° C. [1-[3-[Bis(4-fluorophenyl)amino]propyl]-4-piperidinyl]-(4-chlorophenyl)methanone ethanedioate shows approximately 8% inhibition of ³H-haloperidol binding at 10 n moles concentration and approximately 69% inhibition of ³H-haloperidol binding at 100 n moles concentration in the ³H-Haloperidol Receptor Binding Assay.

EXAMPLE 45

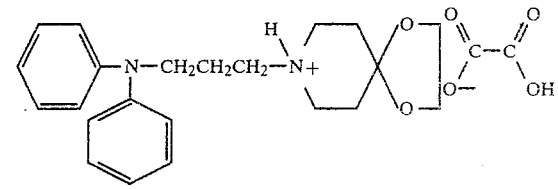

N,N-diphenyl-1,4-dioxo-8-azaspiro[4,5]decane-8-propanamine ethanedioate.

A mixture of 62.7 g. (0.216 moles) of 3-[N,N-diphenylaminopropyl]-1-bromopropane, 30.9 g. (0.216 moles) of 1,4-dioxa-8-azaspiro[4,5]decane (available from the Aldrich Chemical Company, Milwaukee, Wis.), 22.9 g. (0.216 moles) of sodium carbonate, and 1.2 g. of sodium iodide in 250 ml. of toluene is refluxed for about 16 hours, cooled, washed with water and shaken with 5% hydrochloric acid. The bottom oily layer which forms is collected and shaken with chloroform and dilute caustic. The chloroform layer is chromatographed on a column of silica gel, eluting with chloroform. The product fractions are combined and evaporated to give 35.2 g. of an oil. A 5 g. portion of this oil is crystallized in isopropanol, which contains an excess of oxalic acid, to give 6.0 g. of N,N-diphenyl-1,4-dioxa-8-azaspiro[4,5]decane-8-propanamine ethanedioate (1:1), mp. 189°–190.5° C. N,N-diphenyl-1,4-dioxo-8-azaspiro[4,5]decane-8-propanamine ethanedioate shows approximately 10% inhibition of ³H-haloperidol binding at 10 n moles concentration and approximately 26% inhibition of ³H-haloperidol binding at 100 n moles concentration in the ³H-Haloperidol Receptor Binding Assay.

EXAMPLE 46

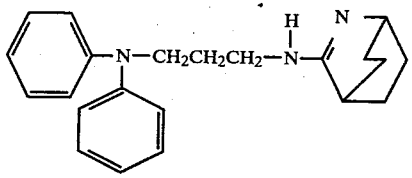

N'-2-azabicyclo[2,2,2]-oct-2-en-3-yl-N,N-diphenyl-1,3-propanediamine

A mixture of 100 g. (0.80 moles) of 3-isoquinuclidone in methylene chloride is added to a mixture of 190 g. (1.00 moles) of triethyloxonium tetrafluoroborate in methylene chloride. The preparation of 3-isoquinuclidone is described at *Organic Synthesis Volume* 5, John Wiley and Sons, New York (1973), pages 670–672. The reaction is then stirred for about 16 hours. 276 g. of potassium carbonate is added. 45 ml. of water is then added dropwise over about a 15 minute interval. The reaction mixture is then filtered, and the filtrate is concentrated. The residue is then twice distilled to give 67 g. of 2-aza-3-ethoxy-bicyclo[2,2,2]oct-2-en, bp. 87°–88° C. at 19 mm. A mixture of 3.65 g. (0.0161 moles) of N-[3-(N,N-diphenylamino)propyl]-amine hydrochloride, and 4.94 g. (0.0322 moles) of 2-aza-3-ethoxybicyclo[2,2,2]oct-2-en in 60 ml. of ethanol is heated for about 22 hours on a steambath, allowing solvent to boil away and shielding the reaction mixture from moisture. For about the last six hours, a vacuum is applied to the reaction mixture. The residual reaction product is dissolved in water and washed with ether. The aqueous layer is made basic with caustic. The resulting white crystals are filtered and twice recrystallized from carbon tetrachloride to give 2.8 g of N'-2-azabicyclo[2,2,2]-oct-2-en-3-yl-N,N-diphenyl-1,3-propanediamine, mp. 148.0°–149.5° C.

N'-2-azabicyclo[2,2,2]-oct-2-en-3-yl-N,N-diphenyl-1,3-propanediamine shows approximately 3% inhibition of ³H-haloperidol binding at 10 n moles concentration and approximately 12% inhibition of ³H-haloperidol binding at 100 n moles concentration in the ³H-Haloperidol Receptor Binding Assay.

I claim:
1. A compound having the structural formula II

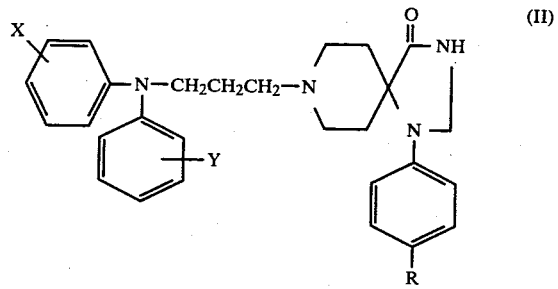

wherein X is hydrogen, halogen, lower alkyl or nitro; Y is hydrogen, halogen, lower alkyl or nitro; R is hydrogen, halogen, lower alkyl, or lower alkoxy; and the non-toxic, pharmaceutically acceptable salts thereof.

2. The compound of claim 1 which is 8-[3-(bis-[4-fluorophenyl)amino)propyl]-1-phenyl-1,3,8-tarizaspiro[4,5]decan-4-one and the non-toxic pharmaceutically acceptable salts thereof.

3. The compound of claim 1 which is 8-[(3-diphenylamino)propyl]-1-(4-fluorophenyl)-1,3,8-triazaspiro[4,5]decan-4-one and the non-toxic pharmaceutically acceptable salts thereof.

4. The compound of claim 1 which is 8-[3-(diphenylamino)propyl]-1-(4-methylphenyll)-1,3,8-triazaspiro[4,5]-decan-4-one and the non-toxic pharmaceutically acceptable salts thereof.

5. The compound of claim 1 which is 8-[3-(diphenylamino)propyl]-1-(4-methoxyphenyl)-1,3,8-triazaspiro[4,5]decan-4-one and the non-toxic pharmaceutically acceptable salts thereof.

6. The compound of claim 1 which is 8-[3-[bis-(4-fluorophenyl)amino]propyl]-1-(4-fluorophenyl)-1,3,8-triazaspiro[4,5]decan-4-one and the non-toxic pharmaceutically acceptable salts thereof.

7. A composition for treating schizophrenia and related ailments in a mammal consisting essentially of an anti-schizophrenically effective amount of a compound as defined in claim 1, in combination with a pharmaceutically acceptable carrier.

8. A method for treating schizophrenia and related ailments in a mammal in need of such treatment; which comprises administering an amount effective for treating the mammal for schizophrenia and related ailments of the composition defined in claim 7 to the mammal.

* * * * *